(12) United States Patent
Cameron

(10) Patent No.: US 7,245,952 B2
(45) Date of Patent: Jul. 17, 2007

(54) NONINVASIVE BIREFRINGENCE COMPENSATED SENSING POLARIMETER

(75) Inventor: Brent D. Cameron, Toledo, OH (US)

(73) Assignee: The University of Toledo, Toledo, OH (US)

( * ) Notice: Subject to any disclaimer, the term of this patent is extended or adjusted under 35 U.S.C. 154(b) by 164 days.

(21) Appl. No.: 11/034,091

(22) Filed: Jan. 12, 2005

(65) Prior Publication Data
US 2005/0154269 A1 Jul. 14, 2005

Related U.S. Application Data

(60) Provisional application No. 60/536,288, filed on Jan. 13, 2004.

(51) Int. Cl.
*A61B 5/00* (2006.01)
(52) U.S. Cl. .............. 600/319; 600/310; 600/316
(58) Field of Classification Search ............ 600/316, 600/318, 319, 310, 322
See application file for complete search history.

(56) References Cited
U.S. PATENT DOCUMENTS

| | | | |
|---|---|---|---|
| 5,209,231 A * | 5/1993 | Cote et al. ................. | 600/310 |
| 5,303,709 A | 4/1994 | Dreher et al. | |
| 5,788,632 A * | 8/1998 | Pezzaniti et al. ........... | 600/316 |
| 6,246,893 B1 * | 6/2001 | Gobeli ...................... | 600/318 |
| 6,356,036 B1 | 3/2002 | Zhou | |
| 6,370,407 B1 * | 4/2002 | Kroeger et al. ............. | 600/319 |
| 6,704,106 B2 | 3/2004 | Anderson et al. | |
| 2003/0223064 A1 * | 12/2003 | Anderson et al. ........... | 356/364 |
| 2003/0225321 A1 * | 12/2003 | Cote et al. ................. | 600/318 |
| 2003/0233036 A1 * | 12/2003 | Ansari et al. .............. | 600/316 |

* cited by examiner

*Primary Examiner*—Eric F. Winakur
(74) *Attorney, Agent, or Firm*—MacMillan, Sobanski & Todd, LLC

(57) ABSTRACT

The present invention relates to a system and method for compensating for the effects of birefringence in a given sample and employs an optical birefringence analyzer to sense the real-time birefringence contributions and then provides a feedback signal to a compound electro-optical system that negates the birefringence contributions found in the given sample. The birefringence contribution vanishes, thus significantly reducing the main error component for polarimetric measurements.

60 Claims, 13 Drawing Sheets

0    π/4    π/2    3π/4    π

L - Laser   P - Polarizer
A - Analyzer   D - Detector
C - Cornea model
BC - Birefringence compensator
FM - Faraday modulator
FC - Faraday compensator

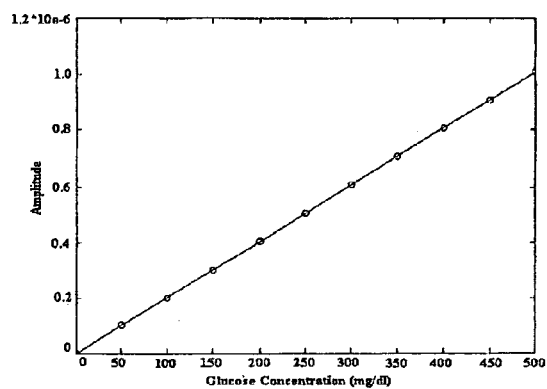 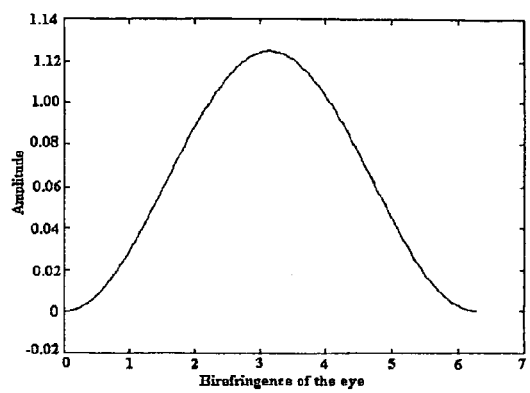
Fig. 7a     Fig. 7b
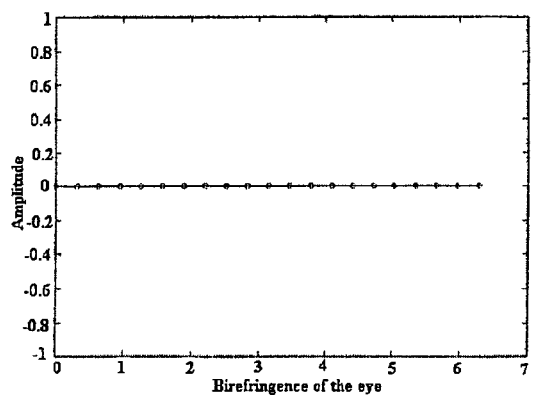
Fig. 7c

NONINVASIVE BIREFRINGENCE COMPENSATED SENSING POLARIMETER

CROSS REFERENCE TO RELATED APPLICATIONS

This application claims the benefit of U.S. provisional patent application Ser. No. 60/536,288 filed Jan. 13, 2004.

FIELD OF INVENTION

The present invention relates to a birefringence compensated sensing polarimetric system. In one aspect, the polarimeter system is used to measure and compensate for corneal birefringence when measuring glucose levels in a patient's eye.

BACKGROUND OF THE INVENTION

Diabetes Mellitus is a common and serious chronic disease, which afflicts about 177 million people worldwide, 17 million people in the United States and is the fourth leading cause of death. It leads to long-term complications such as coronary artery disease, hypertension, retinopathy, neuropathy and nephropathy. Research indicates that self-monitoring of blood glucose levels prevents or slows down the development of these long term complications. An optical polarimetric glucose sensor provides a means for the noninvasive measurement of glucose concentration, thereby reducing pain and complications associated with the current invasive methods.

The use of polarimetry in the detection of analyte concentration has existed for several years. Pohjola demonstrated that glucose concentration in the aqueous humor of the eye is correlated to that of blood. In 1982 March et al. were the first to propose the use of polarimetry to indirectly estimate blood glucose levels via the aqueous humor of the eye. They found in order to measure millidegree sensitive rotations due to glucose at physiological levels a very sensitive and stable polarimeter is required. In the past decade considerable work has been done in the development of such a polarimeter. Coté et al. reported on the potential of millidegree sensitivity by utilizing a true phase technique. This work was later followed by Cameron et al. who reported on a Faraday based polarimeter using a digital closed-loop feedback technique with sub-millidegree sensitivity. Since then, different polarimetric variations have been illustrated by several groups to measure glucose concentration. Chou et al. reported on a polarimeter utilizing an optical heterodyne approach with the ability to detect glucose levels below 10 mg/dl; however, the open loop system lacked stability due to fluctuations in the laser intensity and noise. Most recently, Ansari et al. proposed a theoretical model using the Brewster's reflection off the eye lens for measuring glucose concentration.

Though aqueous humor of the eye contains glucose, it also has other optically active components that can contribute to the overall optical rotation. To estimate glucose concentration in the presence of other optically active components, King et al. demonstrated the use of a multi-spectral Pockels cell based system. This work was followed by Cameron et al. who used a multi-spectral Faraday-based system which also demonstrated the potential to overcome rotations due to the presence of other optically active components. Though glucose concentration in the aqueous humor correlates to that of blood, there is a transport time delay between the diffusion of glucose from the blood into the aqueous humor. If such measurements are to be of benefit to a diabetic person as a reliable predictor of blood glucose concentration, the time delay should be below 10 minutes. In 2001, Cameron et al. measured the transport time delay in a rabbit model and had shown this delay to be under the 10 minute threshold. Most recently, Baba et al. have shown the effects of temperature and pH to be negligible in the normal physiological range.

The main problem currently hindering the development of a viable polarimetric system to indirectly measure blood glucose levels in the aqueous humor of the eye is the birefringence of the cornea associated with motion artifact. Since the birefringence of the cornea is spatially varying, as the cornea moves with respect to the sensing light beam, this motion induced time varying birefringence tends to mask the detected glucose signal.

To date, time varying corneal birefringence due to motion artifact is the main factor limiting in vivo polarimetric glucose measurements in the eye which is not addressed by current glucose sensing polarimeters. U.S. Pat. No. 5,303,709 disclosed a system to facilitate diagnosis of retinal eye disease. To minimize effects of corneal birefringence, this system utilized a backscattered beam from the retina coupled to a variable retarder to reduce corneal birefringence contributions on nerve fiber retinal layer measurements. The compensation implementation in the '709 patent incorporated a polarization sensitive confocal system integrated into a scanning laser retinal polarimeter. U.S. Pat. No. 6,704,106 disclosed a method and system to cancel retardance error in regards to retinal nerve fiber layer measurements. To achieve this, four retardance measurements collected over one complete rotation of a mechanically rotated half-wave retarder are averaged to minimize effects of system birefringence, leaving a mean retardance measurement free of residual polarization bias. In U.S. Pat. No. 6,356,036, a system and method for determining birefringence on the anterior segment (i.e. cornea and lens) of a patient's eye was disclosed. This method involved using a backscattered (i.e. reflected) light beam similar to that disclosed in '709 except the patient's lens reflection intensity through confocal imaging is no longer used as a reference and birefringence of all segments of the eye that are anterior to the retina are determined using a direct polarization beam. In other words, '036 eliminated the need for a confocal imaging system and the scanning laser polarimeter was now able to use the same path to measure birefringence of the anterior segment of the eye. In regards to the invention disclosed herein, a propagated polarized laser beam, not backscattered, passes directly through the anterior chamber of the eye and does not interact with the lens or retina. In addition, the compensator is tied to an autonomous controller system to compensate for corneal birefringence effects in real-time.

Accordingly, it is an object of the present invention to provide an improved noninvasive glucose sensing polarimeter that incorporates a new method to overcome the effects of corneal birefringence, therefore, allowing for the realization of in vivo polarimetric glucose measurements. In addition, such an implementation as described herein would allow for the detection of any optically active molecule in a medium or sample in which birefringence is a problem. Furthermore, the approach to birefringence compensation could be implemented in most types of optical polarimeters, other than the Faraday approach as described herein.

The prior art fails to provide any practical, workable polarimeter system which can consistently provide accurate measurements of the glucose level in human tissue. There is a strong but unmet need for a practical, reliable system which overcomes the problems of the prior art to provide a noninvasive system for measurement of human glucose levels.

Some prior art systems are not noninvasive and certain polarimetric based systems, used for analyte sensing, are not birefringence compensated. The systems do not employ a birefringence compensator, nor do they sense real-time corneal birefringence. The ability to sense and compensate for birefringence effects allows for analyte measurements regardless of light path (i.e. location).

DISCLOSURE OF THE INVENTION

The present invention relates to a system and method for compensating for the effects of birefringence and employs an optical birefringence analyzer to sense the real-time corneal birefringence contributions and then provides a feedback signal to a compound electro-optical system that negates the contributions found is a given sample. The birefringence contribution vanishes, thus significantly reducing the main error component for polarimetric measurements.

In one aspect, the present invention relates to a birefringence sensing polarimetric system comprising a means for measuring rotation of a substance in a sample, and a means for computing the value of retardance that need to be applied at a birefringence compensator in order to eliminate any rotation of a polarization vector due to the sample.

In certain embodiments, the rotation measuring means comprises at least one Faraday modulator, at least one Faraday compensator, at least one analyzer, at least one detector, at least one amplifier, and at least one controller. Also, in certain embodiments, at least one means for computing the value of retardance that needs to be applied to the birefringence compensator comprises at least one circular analyzer, at least one detector, and at least one controller. The retardance is computed and sent as an input into a compensation portion of the controller wherein the compensation algorithm can be represented by the difference equation: $y(n) = x(n) + y(n-1)$ where 'y' is the retardance applied to the birefringence compensator and 'x' is the computed retardance, and wherein upon completion, there is no circularly polarized component and only linearly polarized light and any birefringence is compensated for.

In another aspect the present invention relates to a method for overcoming corneal birefringence comprising: using a circular Stokes parameter 'V' for measuring birefringence compensation, and measuring glucose concentration using a Faraday based glucose sensing polarimeter.

In yet another aspect, the present invention relates to a non-invasive in vivo method for sensing a concentration of an optically active substance in an animal's aqueous humor. The method comprising: aligning a polarizer with a fast axis of the initial retarder to minimize effects of anterior corneal birefringence wherein a polarized laser beam passes through the glucose sample and the posterior corneal surface with a retardance ($\delta$), and splitting the laser beam wherein, in order to compensate for the posterior birefringence before determining glucose rotation, output light from the sample and retarder is separated into two paths by the beam splitter such that one beam is passed through an analyzer capable of characterizing at least one of four Stokes parameters (I,Q, U,V), and receiving a second of the split beams in a modulator and modulating the linear polarization vector of the laser.

BRIEF DESCRIPTION OF DRAWINGS

FIG. 7a is a graph showing detected amplitude versus glucose concentration without corneal birefringence.

FIG. 7b is a graph showing detected amplitude versus corneal birefringence for a fixed glucose concentration without compensation.

FIG. 7c is a graph showing detected amplitude versus corneal birefringence for a fixed glucose concentration and birefringence compensation.

FIG. 10a—without any glucose solution; FIG. 10b—with a glucose concentration of 200 mg/dl; and FIG. 10c—with a glucose concentration of 200 mg/dl and retardance of 5 degrees.

BEST MODE OF CARRYING OUT THE INVENTION

Figure 1:
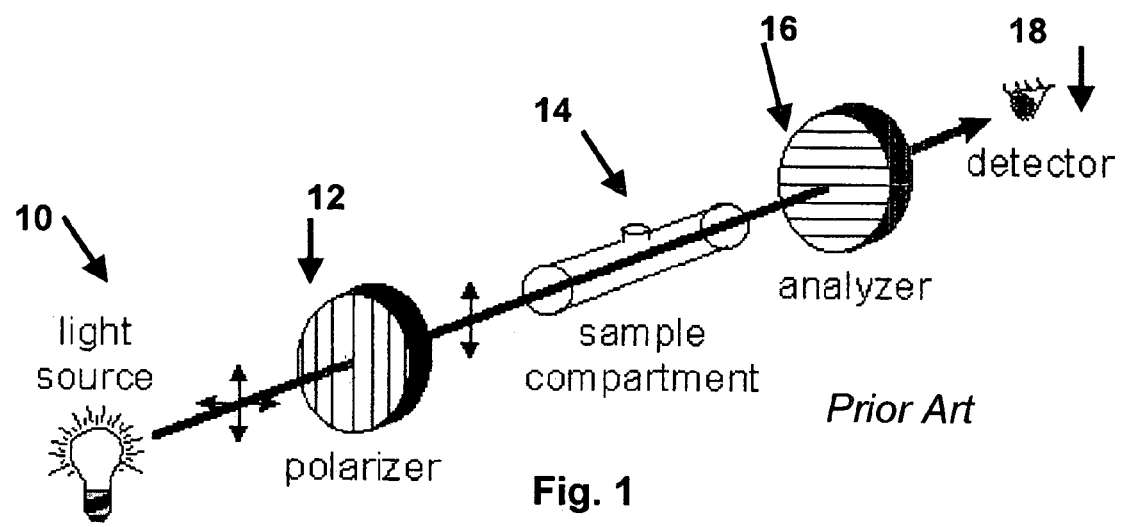
FIG. 1 is a prior art schematic illustration of a simple polarimeter.

In one aspect of the present invention, optical polarimetry is applied to the development of a noninvasive glucose sensor. Optical polarimetry relies on the optical activity of glucose to rotate the linear polarization of light that is proportional to concentration. The glucose concentration in the aqueous humor contained within the anterior chamber of the eye provides an indirect measure of blood glucose concentration. The glucose concentration in the aqueous humor of the eye is correlated with that of blood. In order to measure millidegree sensitive rotations due to glucose at physiological levels, a very sensitive and stable polarimeter is required.

One problem with using the aqueous humor of the eye as the sensing site is that it has other optically active components that could contribute to the overall optical rotation. Other optically active components that may be included in the aqueous humor of the eye include the latic acid, albumin and the like. For a given substance, wavelength, ORD characteristics and molecular make-up of these samples need to be calculated. These relationships are described in the following pages of this specification. The other problem with using the aqueous humor as the sensing medium is the transport time delay between the diffusion of glucose from the blood into the aqueous humor. If such measurements are to be of benefit to a diabetic person as a reliable predictor of blood glucose concentration, the time delay should be below 10 minutes. Still another problem currently hindering in vivo polarimetric glucose detection with the eye as the sensing site is the birefringence of the cornea associated with motion artifact. The cornea is a birefringent material and the birefringence varies as a function of the corneal position. This corneal birefringence associated with motion artifact alters the state of polarization of the input beam, thus, masking the glucose signature.

The present invention relates to a system and a method which overcome the variations in the birefringence of the cornea. In addition, the inventive system described herein compensates for corneal birefringence and the azimuthal angle of the fast and slow corneal optical axes.

Specific Rotation

A beam of light is composed of electromagnetic waves oscillating perpendicular to direction of light propagation. Normally, light exists in an unpolarized state. Unpolarized light has electromagnetic oscillations that occur in an infinite number of planes. A device known as a linear polarizer only transmits light in a single plane while eliminating or blocking out light that exists in other planes. The light exiting the polarizer is known as plane polarized light.

Chiral organic molecules are molecules that do not contain a structural plane of symmetry. They rotate the polarization plane of light as it propagates through the sample. These molecules are collectively known as optically active. Depending on the molecules' confirmation, the plane of polarization may either be rotated clockwise or counter-clockwise. Molecules possessing the ability to rotate light to the left or counter-clockwise are denoted as levorotatory (L−) and those that rotate light to the right or clockwise are referred to as dextrorotatory (D+). Glucose is a dextrorotatory optically active molecule. The specific rotation of glucose dissolved in water is +52.6°/(dm g/ml).

The equation which relates optical rotation to a molecules specific rotation is given by equation (1)

$$[\alpha]_{\lambda,pH}^{T} = \frac{100\alpha}{LC} \quad (1)$$

Where $[\alpha]_{\lambda,pH}^{T}$ is the specific rotation of an optically active compound, $\alpha$ is the observed rotation in degrees, L is the path length in dm, and C is the sample concentration in grams of mass per ml of solution.

For a given chiral substance, the wavelength dependence of specific rotation provides the Optical Rotatory Dispersion (ORD) characteristics of the constituent molecule. Every optically active molecule possesses its known unique ORD curve based on its molecular makeup.

$$[\alpha] = \frac{k_0}{\lambda^2 - \lambda_0^2} \quad (2)$$

The relationship between wavelength and specific rotation is given by Drude's equation. Equation (2) is an approximation of Drude's equation and is valid only outside the absorption region for the molecule of interest. If the specific rotation of a chiral molecule is known at two different wavelengths, equation (2) can be solved for $k_0$ and $\lambda_0$ and the specific rotation can be calculated for any wavelength within the region. Other tissue of the body may be used as sensing sites. Tissues of ear, nose and the thin skin areas between fingers and toes may be sensed. These are non-bony tissues. If used, wavelength and molecular makeup will have to calculate for these sensing sites.

Polarimetry

The optical instrument used to measure rotation due to an optically active sample is a polarimeter. The main components of a polarimeter are a light source 10, a polarizer 12, a sample cell container 14, a second polarizer 16 known as the analyzer, and a detector 18, as shown in FIG. 1.

As the beam passes through the sample, the plane of polarization will rotate according to the concentration of the sample and path length of the container. The amount of rotation due to the sample can be determined using the analyzer. If the analyzer is oriented perpendicular to the initial polarizer, theoretically no light will be transmitted if a sample is present. If an optically active sample is then introduced into the system, the intensity of transmitted light will be proportional to the amount of rotation in polarization due to the sample. Thus, the detected light intensity is related to the sample's concentration assuming a constant path length.

Polarimetry and the Eye as the Sensing Site

For in vivo polarimetric glucose detection, a suitable sensing site is required. Several tissues in the body, such as the skin, are extremely scattering in nature. This scattering effect tends to significantly depolarize the light making it difficult to measure the small rotations due to physiological glucose levels. The eye is unique in that the cornea provides a low scattering window into the body. The diffusion or secretion of glucose into the aqueous humor of the eye correlates with blood glucose levels with a time delay. These reasons make the eye a preferred sensing site.

Although the eye is virtually void of scatter and has a glucose concentration correlated to blood, it also has its own drawbacks as a sensing site. The main drawback is the spatially varying birefringence of the cornea associated with motion artifact.

Corneal Birefringence

If the optical properties of a substance are same in all the directions regardless of its orientation, the substance is said to be isotropic. In many crystalline structures and some organic substances the optical properties are not the same in all directions and they have more than one index of refraction and these materials are known as anisotropic.

Figure 2:
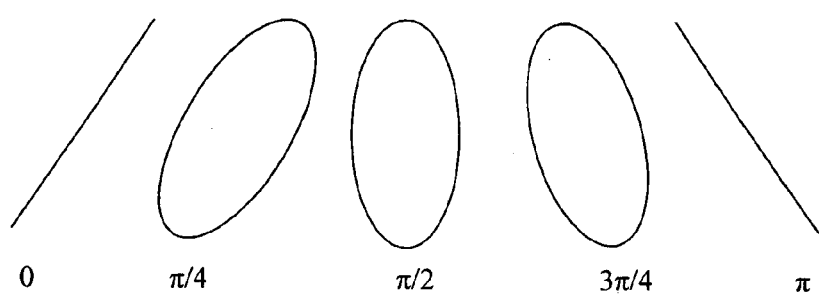
FIG. 2 is an illustration of linear to elliptical polarization states with varying retardance.

Birefringence is a property of anisotropic substances in which two orthogonally oriented different refractive indices of light exist, the ordinary refractive index, $\eta_o$ (along the slow axis) and extraordinary refractive index $\eta_e$ (along the fast axis). Light that is polarized along the x-axis experiences a different index of refraction, and therefore travels at a different speed than does light polarized along the y-axis. This difference in the speed of propagation between the x and y polarized components induces a phase difference. Depending on the magnitude of the components and the relative phase retardance (δ), different states varying from linear to elliptical are shown in FIG. 2.

The cornea is a birefringent an isotropic substance. Corneal birefringence is due to stroma that are composed of sheets of lamellae which are further composed of collagen fibers aligned parallel to each other. Each successive sheet of lamella is oriented differently with respect to the previous layer. Each of these layers contains its own inherent birefringence and the degree of the arrangement of the lamella determines the overall birefringence. In many studies it has been shown that magnitude of retardation increases along the radius towards the periphery of the cornea. Birefringence of the cornea associated with the motion artifact is the major problem currently hindering in vivo polarimetric glucose measurements.

Digital Closed Loop Controlled Glucose Sensing Polarimeter

Figure 3A:
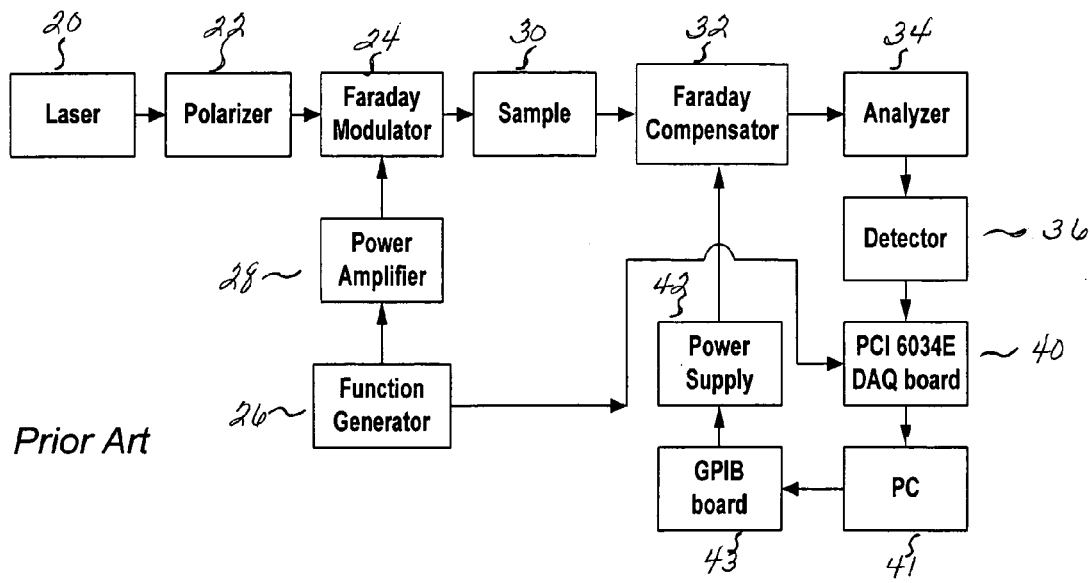
FIG. 3a is a schematic illustration of a digital closed-loop controlled glucose sensing polarimeter.

The block diagram of the system used for in vitro glucose detection is shown in FIG. 3a (prior art). A diode laser 20 emitting 1 mW of power at a wavelength of 670 nm (red) is used as a light source. The laser beam is polarized by an initial polarizer 22 present in the optical system. Modulation of the polarization vector is provided by a Faraday modulator 24 driven by a sinusoidal function generator 26 at a frequency of 804 Hz and modulation depth of ±1°. In certain embodiments, a power amplifier 28 can be used between the function generator 26 and the Faraday modulator 24. This modulated signal propagates through a sample cell container 30 constructed of optical grade glass with a path length of 1 cm. A Faraday compensator 32 is then used to provide feedback compensation within the system. The purpose of this compensator 32 is to nullify or eliminate any rotation due to glucose. Following the Faraday compensator 32 is another polarizer 34 which functions as an analyzer. The analyzer 34 transforms the modulated polarization vector into intensity modulation according to Malus' law. The intensity is detected by a silicon photo diode detector 36 and amplified by a wide bandwidth amplifier (not shown) which outputs a voltage proportional to the detected light intensity. The amplified output and modulation signal are sent as inputs to a lock-in amplifier and controller program through a data acquisition (DAQ) board. In certain embodiments, the controller program is connected to a PC 41, which, in turn, is operatively connected to the power supply 42. The lock-in amplifier measures the signal component present at the modulation frequency, and based on this signal, the controller decides the course of action to be taken in order to compensate for any rotation due to the optically active sample. The output of the controller is applied to the Faraday compensator 32 through a GPIB controlled DC power supply 42. This output is used to drive the Faraday compensator 32 to nullify the system.

The intensity of light which is detected by the system is given by equation (3)

$$I = \left(\phi^2 + \frac{\theta_m^2}{2}\right) + 2\phi\theta_m \sin(\omega_m t) - \frac{\phi_m^2}{2}\cos(2\omega_m t) \tag{3}$$

Where $\omega_m$ is the modulation frequency, $\theta_m$ is the modulation depth of the faraday modulator. $\phi$ is the difference in the rotation due to glucose and Faraday compensator. The detected signal consists of a dc term, a frequency-doubled term, and the signal of interest at the modulation frequency $\omega_m$ which is used as the input into the control system.

Stokes/Mueller Model for the Designed Corneal Birefringence Compensation System

Figure 3B:
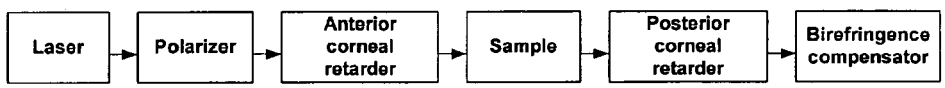
FIG. 3b is a block diagram of a corneal birefringence compensation module.

A generalized block diagram of the corneal birefringence compensation module of the glucose sensing polarimetric system is illustrated in FIG. 3b.

The main components present in the birefringence compensator optical system are a laser, polarizer, retarder (anterior birefringence), sample, retarder (posterior birefringence), and the birefringence compensator. The use of Stokes vector and Mueller matrix theory provides a way to model the system for computing the birefringence. The Stokes/Mueller model for this optical system is given by the following matrix system (eqn 3.1)

$$\begin{bmatrix} I \\ Q \\ U \\ V \end{bmatrix} = \overset{\text{Birefringence compensator}}{\begin{bmatrix} 1 & 0 & 0 & 0 \\ 0 & \cos^2(2\gamma_1) + \sin^2(2\gamma_1)*\cos(\delta_1) & \sin(2\gamma_1)\cos(2\gamma_1)(1-\cos(\delta_1)) & -\sin(2\gamma_1)\sin(\delta_1) \\ 0 & \sin(2\gamma_1)\cos(2\gamma_1)(1-\cos(\delta_1)) & \sin^2(2\gamma_1) + \cos^2(2\gamma_1)*\cos(\delta_1) & \cos(2\gamma_1)\sin(\delta_1) \\ 0 & \sin(2\gamma_1)\sin(\delta_1) & \cos(2\gamma_1)\sin(\delta_1) & \cos(\delta_1) \end{bmatrix}} * \tag{3.1}$$

$$\overset{\text{Posterior retarder}}{\begin{bmatrix} 1 & 0 & 0 & 0 \\ 0 & \cos^2(2\gamma) + \sin^2(2\gamma_1)*\cos(\delta) & \sin(2\gamma)\cos(2\gamma)(1-\cos(\delta)) & -\sin(2\gamma)\sin(\delta) \\ 0 & \sin(2\gamma)\cos(2\gamma)(1-\cos(\delta)) & \sin^2(2\gamma) + \cos^2(2\gamma)*\cos(\delta) & \cos(2\gamma)\sin(\delta) \\ 0 & \sin(2\gamma)\sin(\delta) & \cos(2\gamma)\sin(\delta) & \cos(\delta) \end{bmatrix}} *$$

$$\overset{\text{Sample}}{\begin{bmatrix} 1 & 0 & 0 & 0 \\ 0 & \cos(2\varphi_g) & \sin(2\varphi_g) & 0 \\ 0 & -\sin(2\varphi_g) & \cos(2\varphi_g) & 0 \\ 0 & 0 & 0 & 1 \end{bmatrix}} * \frac{1}{2} \overset{\text{Polarizer}}{\begin{bmatrix} 0.5 & -0.5 & 0 & 0 \\ -0.5 & 0.5 & 0 & 0 \\ 0 & 0 & 0 & 0 \\ 0 & 0 & 0 & 0 \end{bmatrix}} * \overset{\text{Laser}}{\begin{bmatrix} 1 \\ 0 \\ 0 \\ 0 \end{bmatrix}}$$

where the system of matrices are presented in opposite order to the direction of light propagation. 'γ' is the azimuthal angle and 'δ' is the retardance due to the posterior corneal retarder, '$\gamma_1$' is the azimuthal angle and '$\delta_1$' is the retardance due to the birefringence compensator, $\phi_g$ is the rotation due to glucose. This model does not account for the initial retarder as its optical axis is aligned with the initial polarization state. Initially, the birefringence compensator does not compensate for the retardance, therefore, $\gamma_1$ and $\delta_1$ would be zero and the Mueller matrix of the compensator would result in an identity matrix. Since, elliptically polarized light is represented only by the Stokes parameter 'V', simplifying the equation yields:

$$V = \frac{1}{2}[-\sin(\delta)\sin(2\gamma + 2\phi_g)] \quad (3.2)$$

Rearranging terms in equation [3.2], and assuming $\phi_g$ to be negligible for physiological glucose levels, retardance δ is given by:

$$\delta_{predicted} = \sin^{-1}\left[\frac{-2V}{\sin(2\gamma)}\right] \quad (3.3)$$

In the above equation, the Stokes parameter 'V' is detected using a circular analyzer, as described herein.

Stokes/Mueller Model for the Glucose Sensing Polarimetric System

Figure 4A:
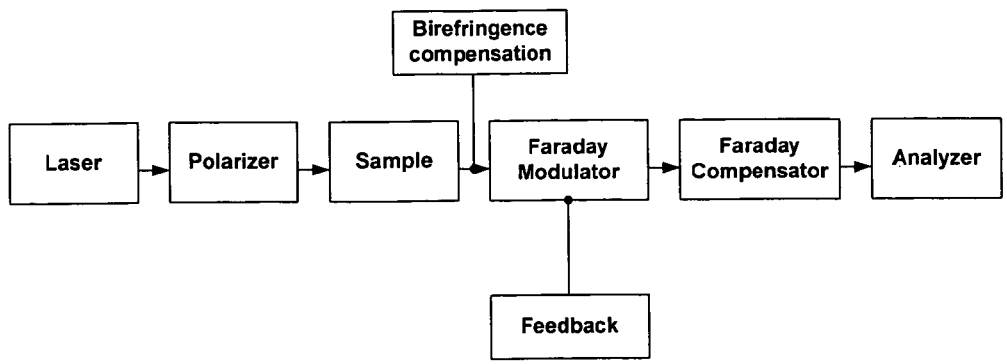
FIG. 4a is a block diagram of a glucose sensing polarimetric system.

The generalized block diagram for the glucose sensing polarimetric system is illustrated in FIG. 4a. The main components present in the optical system of the designed polarimeter are a laser, polarizer, sample, birefringence compensator, Faraday modulator, Faraday compensator, analyzer, and detector. The use of Stokes vector and Mueller matrix theory provides a way to model the polarized light beam throughout the optical system. For glucose sensing, the birefringence compensator cancels out any retardance due to the sample. Therefore, there is end effect is the contributions of the birefringence compensator and sample cancel out, therefore the Mueller matrix combination of these two, result is an identity Mueller matrix. For simplification, eliminating the birefringence compensator and the sample retardance from the optical system, the matrix representation of the system is given by:

$$\begin{bmatrix} I \\ Q \\ U \\ V \end{bmatrix} = \frac{1}{2}\begin{bmatrix} 1 & 1 & 0 & 0 \\ 1 & 1 & 0 & 0 \\ 0 & 0 & 0 & 0 \\ 0 & 0 & 0 & 0 \end{bmatrix} * \begin{bmatrix} 1 & 0 & 0 & 0 \\ 0 & \cos(-2\phi_f) & \sin(-2\phi_f) & 0 \\ 0 & -\sin(-2\phi_f) & \cos(-2\phi_f) & 0 \\ 0 & 0 & 0 & 1 \end{bmatrix} *$$

Analyzer, Faraday Compensator $$\begin{bmatrix} 1 & 0 & 0 & 0 \\ 0 & \cos(-2\theta_m\sin(\omega_m t)) & \sin(-2\theta_m\sin(\omega_m t)) & 0 \\ 0 & -\sin(-2\theta_m\sin(\omega_m t)) & \cos(-2\theta_m\sin(\omega_m t)) & 0 \\ 0 & 0 & 0 & 1 \end{bmatrix} *$$

Faraday Modulator

-continued $$\begin{bmatrix} 1 & 0 & 0 & 0 \\ 0 & \cos(2\phi_g) & \sin(2\phi_g) & 0 \\ 0 & -\sin(2\phi_g) & \cos(2\phi_g) & 0 \\ 0 & 0 & 0 & 1 \end{bmatrix} * \frac{1}{2}\begin{bmatrix} 1 & -1 & 0 & 0 \\ -1 & 1 & 0 & 0 \\ 0 & 0 & 0 & 0 \\ 0 & 0 & 0 & 0 \end{bmatrix} * \begin{bmatrix} 1 \\ 0 \\ 0 \\ 0 \end{bmatrix}$$

Sample, Polarizer, Laser where $\phi_f$ is the rotation in polarization due to the compensation Faraday rotator, $\phi_g$ is the rotation due to the optically active sample, $\theta_m$ is the modulation depth, $\omega_m$ is the modulation frequency and t is the time. This system of matrices when multiplied through can be simplified to the equation below $$\begin{bmatrix} I \\ Q \\ U \\ V \end{bmatrix} = \begin{bmatrix} 1 - \cos(2\varphi_g - 2\varphi_f - 2\theta_m\sin(\omega_m t)) \\ 1 - \cos(2\varphi_g - 2\varphi_f - 2\theta_m\sin(\omega_m t)) \\ 0 \\ 0 \end{bmatrix} \quad (4)$$

Applying the substitution $\phi = \phi_g - \phi_f$ and further simplifying the equation (4) for intensity is given by the equation 5

$$I = \frac{1}{2}[\sin^2(\varphi - \theta_m\sin(\omega_m t))] \quad (5)$$

If the intensity equation (5) is further simplified and the assumption is made that $\sin(x) \approx x$ for $x \ll 1$, the equation above (5) can be reduced to:

$$I = \frac{1}{2}[\varphi^2 - 2\varphi\theta_m\sin(\omega_m t) + \theta_m^2\sin^2(\omega_m t)] \quad (6)$$

Applying the identity $$\sin^2 x = \frac{1}{2} - \frac{1}{2}\cos 2x$$

to the equation above (6) yields, $$I = \frac{\varphi^2}{2} + \frac{\theta_m^2}{4} - \varphi\theta_m\sin(\omega_m t) - \frac{\theta_m^2}{4}\cos(2\omega_m t) \quad (7)$$

The equation above (7) describes the intensity of light, which is detected by the system at any instance of time. As can be seen, the detected signal consists of a DC term, a frequency-doubled term, and the signal of interest at the modulation frequency $\omega_m$, which is used as the input into the control system.

Corneal Birefringence Compensated Glucose Sensing Polarimeter

Figure 4B:
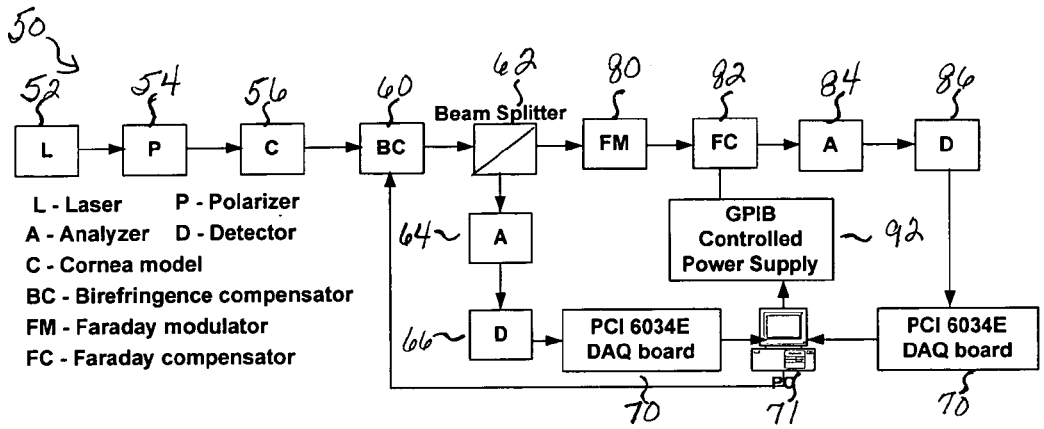
FIG. 4b is a schematic illustration of a corneal birefringence compensated polarimeter using a single birefringence compensator.

FIG. 4b is a schematic illustration of a corneal birefringence compensated polarimeter using a single birefringence compensator. The block diagram of a corneal birefringence compensated glucose sensing polarimeter 50 is shown in FIG. 4b. A light source such as a red diode laser module 52 is used as the light source. The laser 52 is initially polarized by a polarizer 54 and is oriented such that the maximum transmission is obtained. The polarizer 54 is aligned with the fast axis of the initial retarder, which minimizes the effect of birefringence due to the anterior side of the cornea. The polarized laser beam then traverses through a sample 56. The cornea birefringence induces a phase retardance ($\delta$) in the polarized laser beam resulting in a change in the state of polarization from linearly polarized light to elliptically polarized light and masking the signature of glucose. In order to compensate for the birefringence, a birefringence compensator 60, which is another electro-optical retarder, applies a retardance that cancels out any effect due to the sample birefringence.

The value of the retardance that needs to be applied at the birefringence compensator is computed by determining the circularly polarized Stokes parameter 'V'. For calculating this Stokes parameter, the elliptically polarized light is split into two routes by a non-polarizing laser line beam splitter 62. One route passes through a circular analyzer 64, which is a quarter wave plate followed by a 45° linear polarizer, capable of characterizing the circularly polarized Stokes parameter 'V'. This beam is then directed towards a detector 66. The detector output is digitized using a data acquisition board (DAQ) 70. In certain embodiments, this is the input into a feedback controller program implemented using a PC 71. This controller outputs a voltage proportional to the birefringence compensation retardance. The compensation algorithm can be represented by the difference equation $$y(n)=x(n)+y(n-1) \quad (8)$$

where 'y' is the retardance applied to the birefringence compensator and 'x' is the computed retardance. Upon completion, there is no circularly polarized component and only linearly polarized light; therefore, the birefringence due to the posterior side of the cornea is compensated for.

In the other route, the linearly polarized laser beam is used for measuring glucose rotation. A Faraday modulator 80 is then used to modulate the linear polarization vector of the laser. The Faraday modulator 80 is driven by a sinusoidal source at 1058 Hz. A Faraday compensator 82 provides feedback compensation within the system. The purpose of this compensator 82 is to nullify or eliminate any rotation of the polarization vector due to the glucose sample. Following the Faraday compensator 82 is another polarizer 84, known as the analyzer, with its transmission axis oriented perpendicular to that of the initial polarizer 54. The analyzer 84 transforms the modulated polarization vector into intensity modulation according to Malus' law. The beam is then directed towards a photo-detector 86 whose output is a voltage proportional to the detected light intensity. The output of the detector 86 is then amplified by a wide bandwidth amplifier (not shown).

The amplified output and modulation signal are sent as inputs to a lock-in amplifier and controller program through a data acquisition board 70. In certain embodiments, the controller program is operatively connected to the PC 71. The lock-in amplifier measures the signal component present at the modulation frequency, while rejecting low and high frequency electro-magnetic noise. The intensity that impinges on the detector is given by equation (8); it is modeled using Stokes vector and Mueller matrix theory, which is described in detail below.

$$I = \frac{\phi^2}{2} + \frac{\theta_m^2}{4} - \phi\theta_m\sin(\omega_m t) - \frac{\theta_m^2}{4}\cos(2\omega_m t) \quad (9)$$

In equation 9, $\theta_m$ is the modulation depth, $\omega_m$ is the modulation frequency, t is time, and $\phi=\phi_g-\phi_f$ where $\phi_g$ and $\phi_f$ are the rotations in polarization due to the glucose sample and Faraday compensator, respectively. As can be seen from equation (9), the relative amplitude of the sinusoidal term at the modulation frequency is proportional to the rotation due to the glucose sample assuming no compensation ($\phi_f=0$). This is used as the input into the controller, which forces the net rotation in polarization to zero. The output of the controller is applied to the Faraday compensator through a GPIB controlled DC power supply 92. Upon completion, the output voltage of the controller is proportional to the glucose concentration of the sample.

Figure 4C:
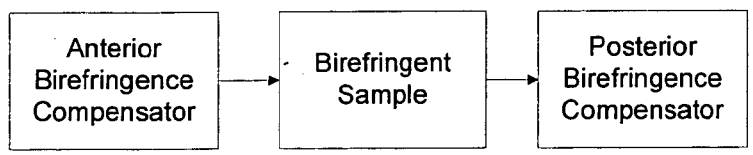
FIG. 4c is a schematic illustration of an expanded birefringence compensator allowing for both anterior and posterior birefringence compensation.
Figure 5A:
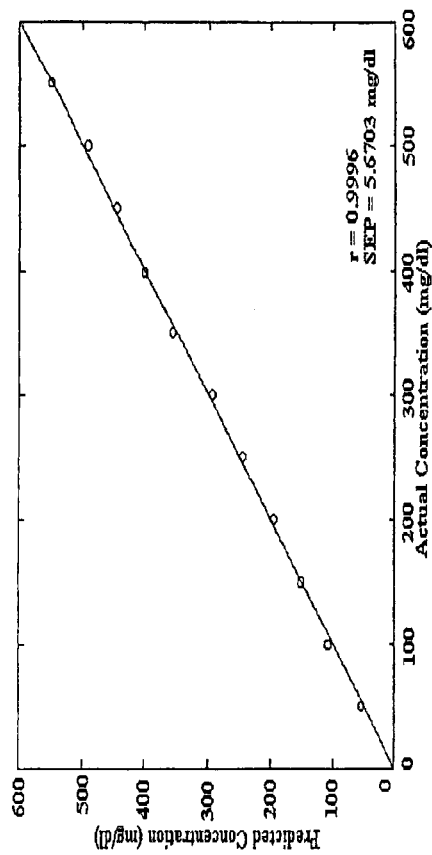
FIGS. 5a–5d are graphs showing actual verses predicted glucose concentrations for hyperglycemic glucose-doped water experiments.
Figure 5B:
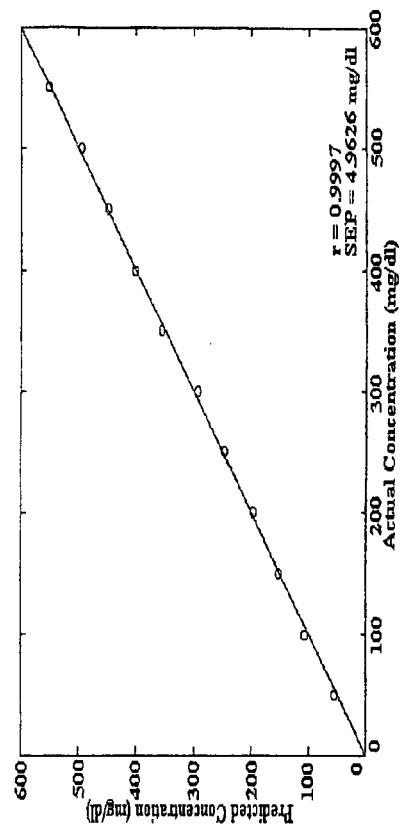
Figure 5C:
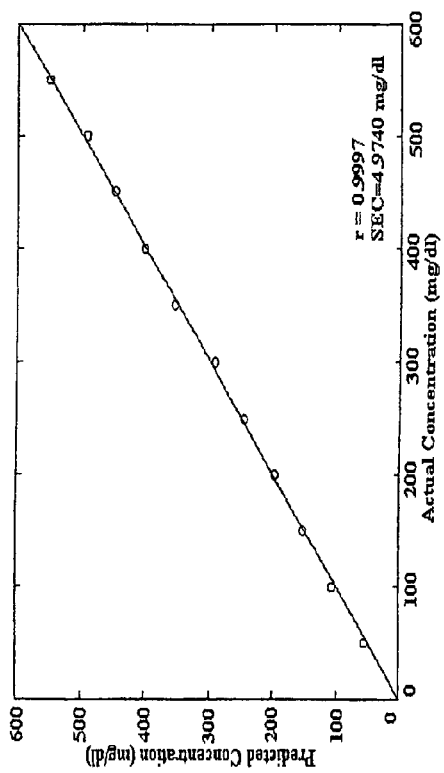
Figure 5D:
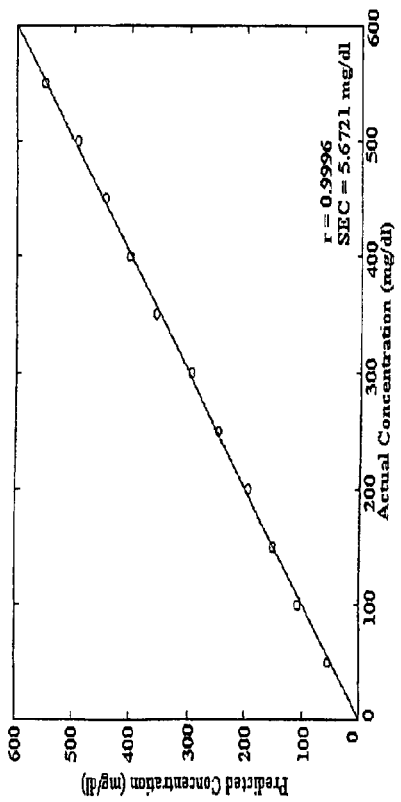
Figure 6A:
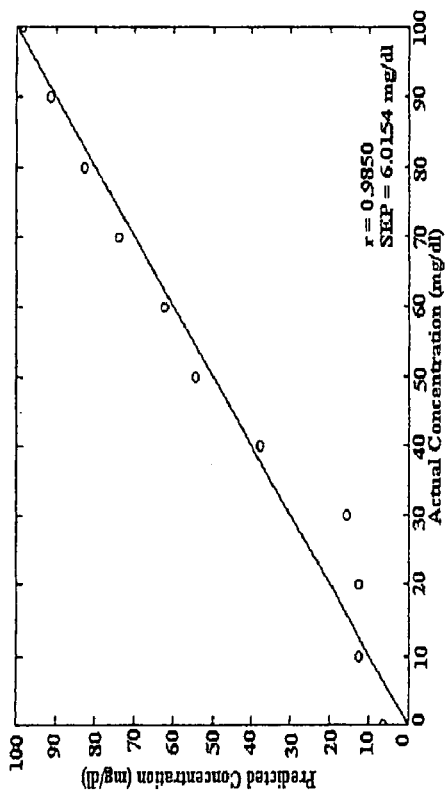
FIGS. 6a–6d are graphs showing actual verses predicted glucose concentrations for hypoglycemic glucose-doped water experiments.
Figure 6B:
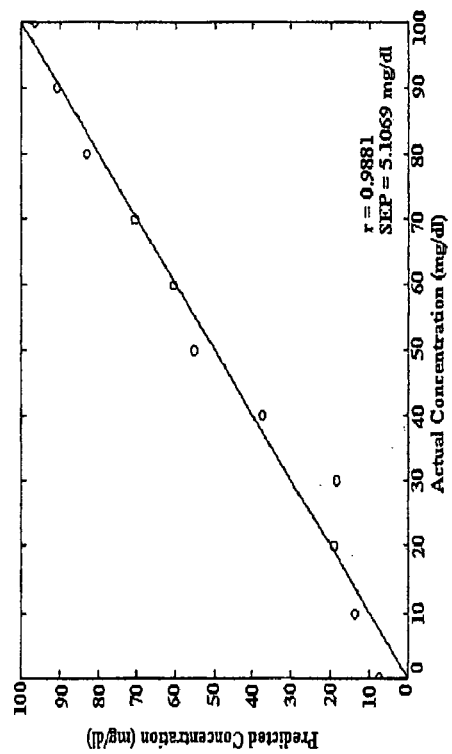
Figure 6C:
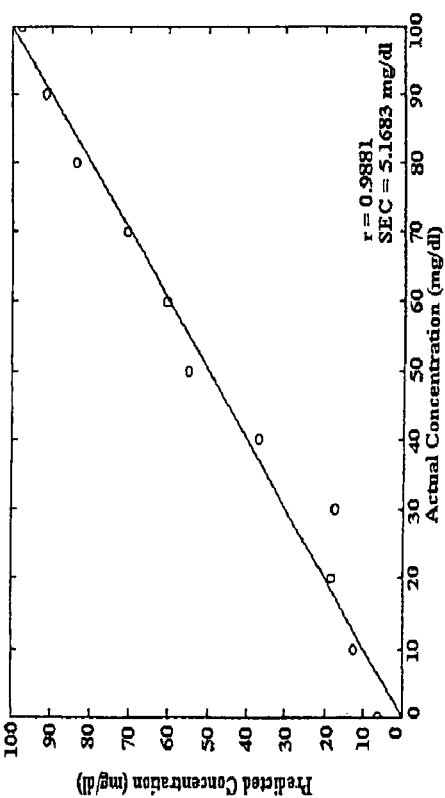
Figure 6D:
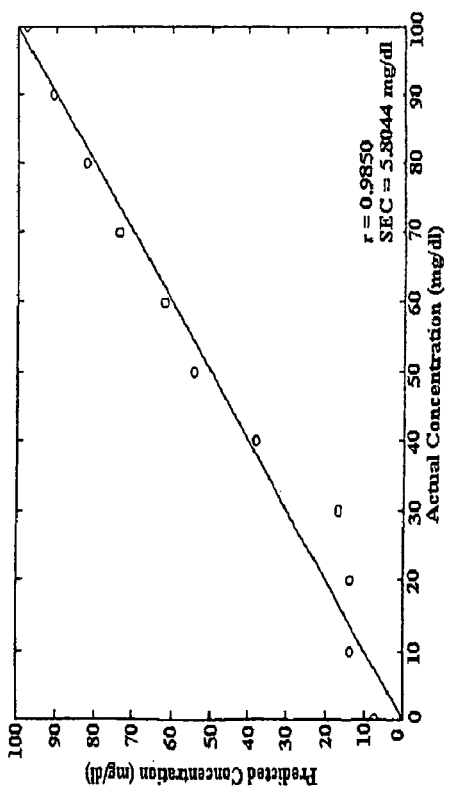

FIG. 4c is a schematic illustration of a more robust implementation of corneal birefringence compensator. In FIG. 4c, instead of using a single birefringence compensator, as illustrated in FIG. 4b, two compensators are implemented to compensate for both anterior and posterior birefringence effects of the sample. Regardless of the compensation approach, the preferred compensation retarder is a liquid crystal retarder, but others may be employed such as a mechanical retarder or a photoelastic modulator (PEM). The path of the polarized laser beam may vary. While a parallel to the segments of the eye are preferred, a path perpendicular or at an angle to retina or lens may be employed.

Real Time Glucose Controller Program

Figure 8:
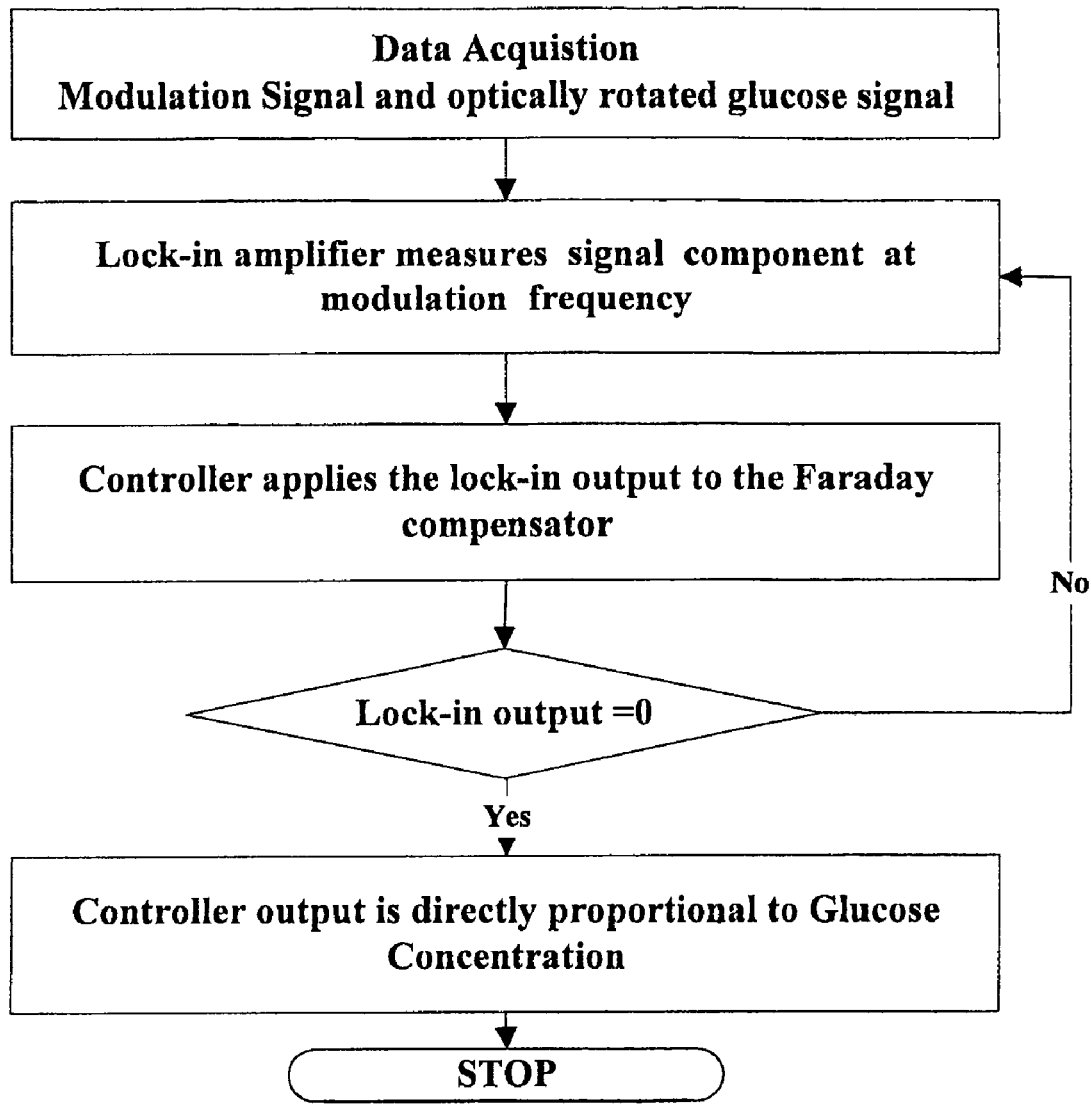
FIG. 8 is a flowchart glucose measurement controller.

The flow chart of the glucose controller program is illustrated in FIG. 8. Lock-in amplifiers are used to detect very small AC signals, and accurate measurements can be made even when the signal is obscured with noise many times larger. They use a technique known as phase sensitive detection to single out the component of the signal at a specific reference frequency and phase. Noise signals at frequencies other than the reference frequency are rejected and do not affect the measurement.

The input signal to the controller program is a signal proportional to the detected optical polarization rotation. The feedback controller applies a voltage proportional to the glucose rotation (i.e. lock-in voltage) to the Faraday compensator, to attempt to negate for the polarization rotation due to glucose. The controller program continues until the lock-in output is sufficiently near zero, which means there is no desired signal component at the modulation frequency. Upon completion, all net optical polarization rotation due to glucose is eliminated; therefore, the output voltage of the controller which is applied to the Faraday compensator is proportional to the glucose concentration of the sample.

EXAMPLE

Experimental Polarimetric Glucose Detection

The Faraday based glucose sensing system was evaluated for zero birefringence contribution for two sets of hyperglycemic 0–600 mg/dl and hypoglycemic 0–100 mg/dl concentration ranges. Least squares linear regression was used to compute a calibration model for glucose prediction. Validation of the calibration model was performed using an independent data set. The actual versus predicted glucose concentrations for both calibration and validation are plotted in FIGS. 5a–d and FIGS. 6a–d, respectively. Each data set possesses a high degree of linearity with all correlation coefficients exceeding r=0.9880. The mean standard error of calibration (SEC) and standard error of prediction (SEP) are 5.4047 mg/dl and 5.4388 mg/dl, respectively.

The birefringence compensated system was simulated for different glucose concentrations varying in steps of 50 from 0–500 mg/dl without a birefringent sample in the optical system. As expected the glucose concentration versus amplitude graph is a linear plot FIG. 7(a). Now, the system was evaluated with the presence of a variable retarder as the sample (e.g. to simulate corneal birefringence); however, without compensating for the birefringence. For this case, the given glucose concentration is fixed at 500 mg/dl and the retardance was varied from 0–2π in steps of 0.01. As can be seen in FIG. 7(b), the detected signal varies with the birefringence which masks the glucose signature. In the ideal case for no corneal birefringence, the curve should be constant for a fixed glucose concentration.

If the retardance due to the cornea is computed from equation (3.3) and is compensated using the birefringence compensator, it can see that the amplitude no longer varies with retardance and is a constant for a given glucose concentration as shown in FIG. 7(c). Therefore, the sample birefringence no longer affects the optical polarization rotation measurement.

EXAMPLE

Figure 9A:
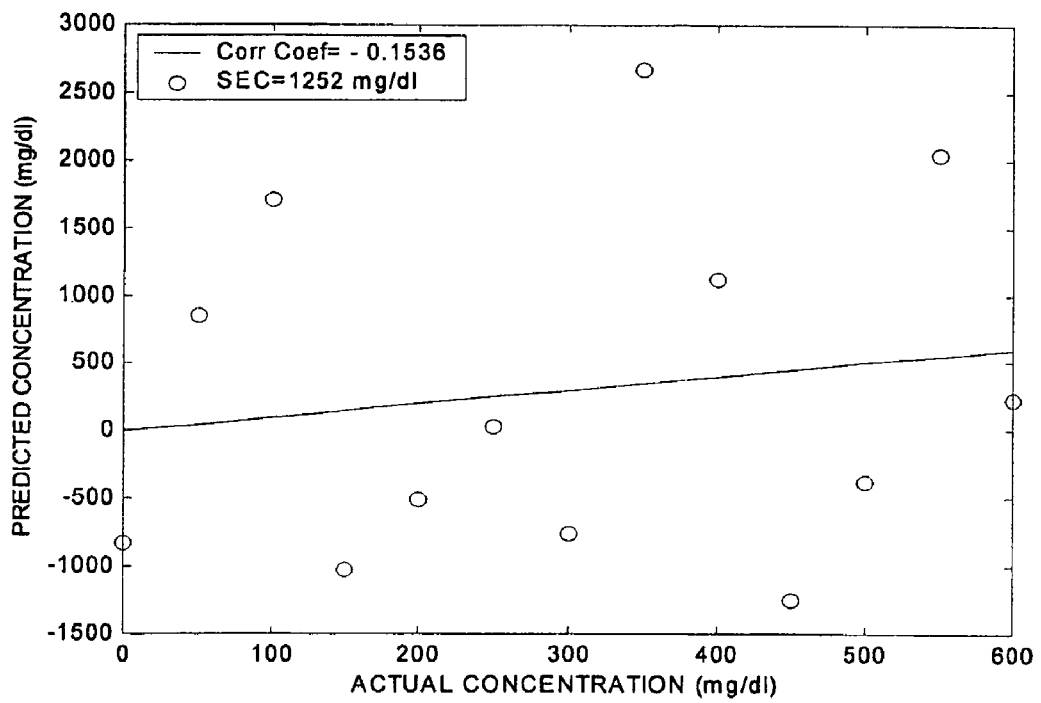
FIGS. 9a and 9b are graphs showing simulation results for uncompensated and compensated hyperglycemic glucose data.
Figure 9B:
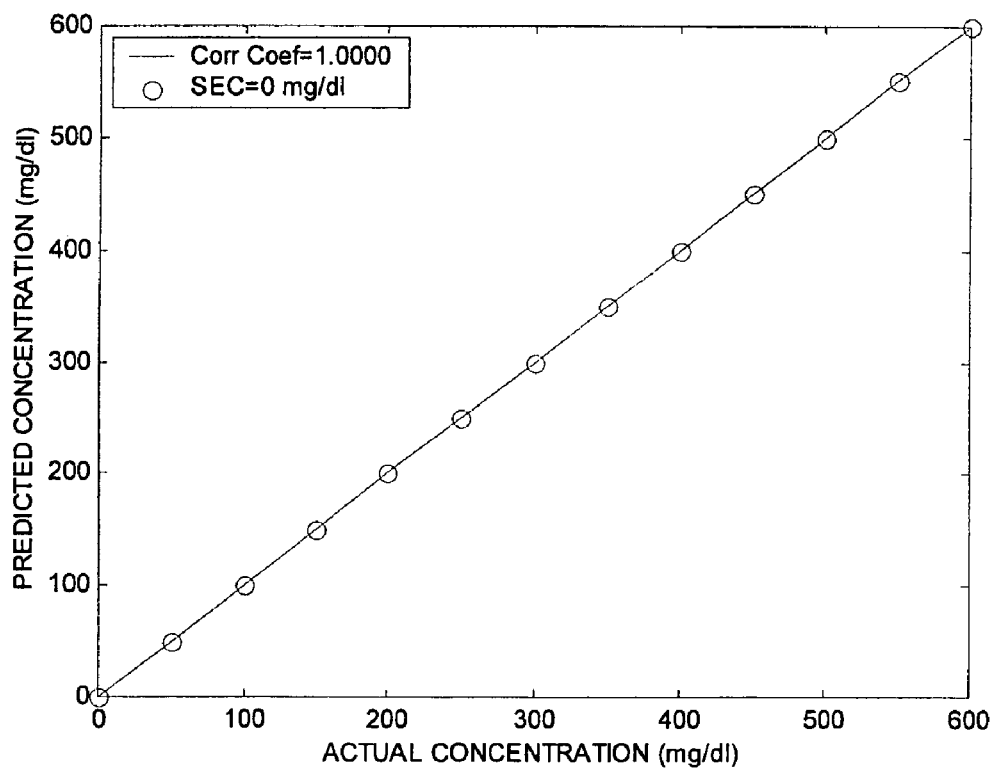

Simulated Noninvasive Corneal Birefringence Compensated Glucose Sensing Polarimeter To better understand the technique employed for corneal birefringence compensation and glucose sensing, the designed system, as depicted in FIG. 4b, was simulated in all aspects. In addition, frequency analysis on the detected signal was performed using the fast Fourier transform (FFT). The simulation program, allowed for the user to arbitrarily change the glucose concentration as well as the amount for corneal birefringence. Furthermore, the simulation has the option of enabling/disabling both the glucose and birefringence controllers separately. The simulation was initially run for different glucose concentrations and retardances. Two sets of experiments were performed using a glucose concentration range of 0–600 mg/dl in increments of 50 mg/dl, one without birefringence compensation and one after birefringence compensation. The retardance values were randomly chosen for different glucose concentrations. The calibration graphs for the uncompensated and compensated data are shown in FIGS. 9a and 9b. As expected, the uncompensated data set possesses a low degree of linearity with the correlation coefficient r=-0.1536. The SEC for the uncompensated and compensated data is 1252 mg/dl and 0 mg/dl respectively. The 1000 fold decrease in the SEC after compensation demonstrates the operation of the presented corneal birefringence compensation method.

EXAMPLE

Corneal Birefringence Masking of Glucose Polarization Rotation

Figure 10A:
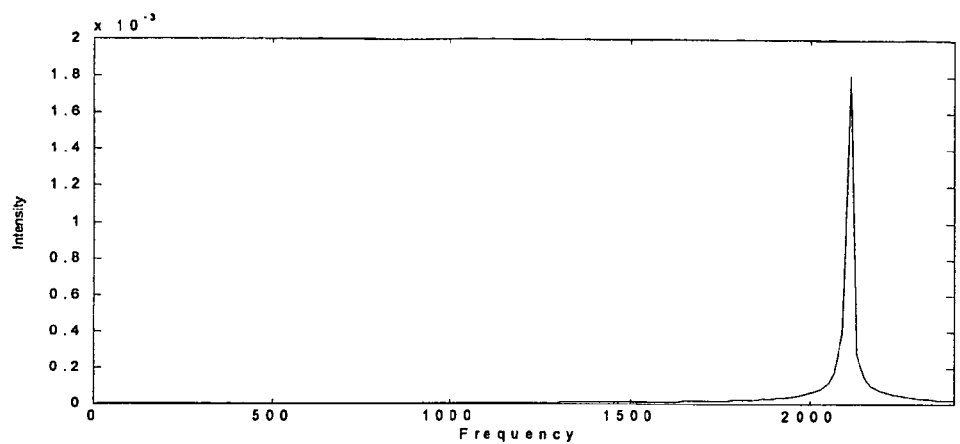
FIGS. 10a, 10b and 10c are FFT graphs that show the effect of glucose rotation and birefringence.
Figure 10B:
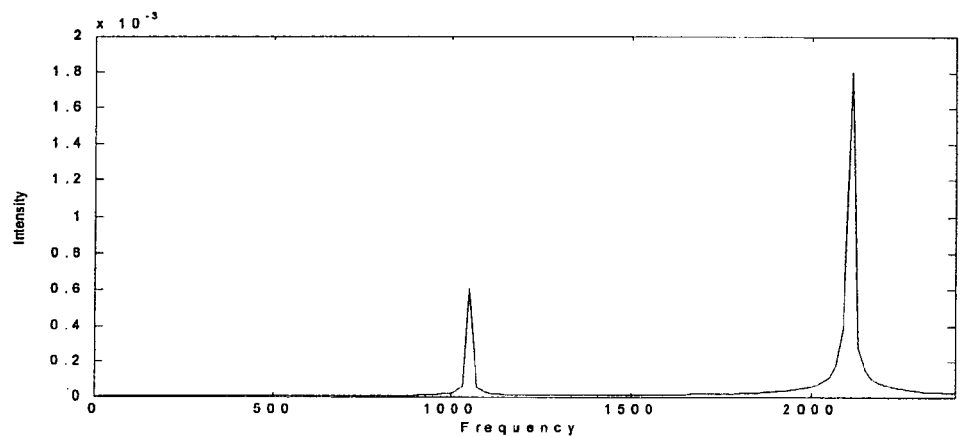
Figure 10C:
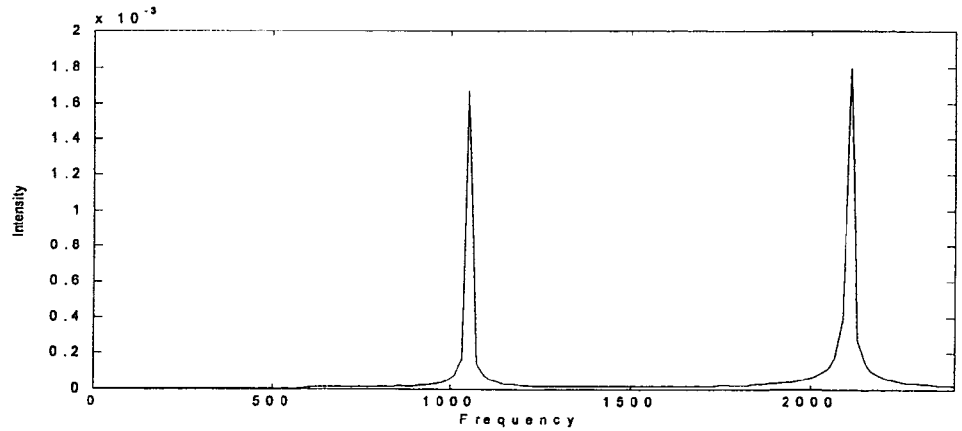
Figure 11A:
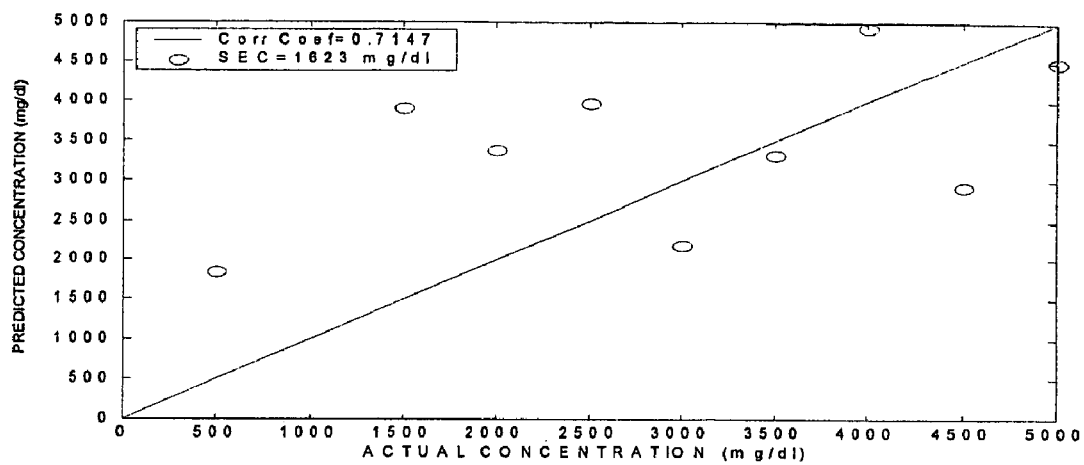
FIGS. 11a, 11b, and 11c are calibration graphs for the uncompensated glucose-doped water experiments (a)–(c).
Figure 11B:
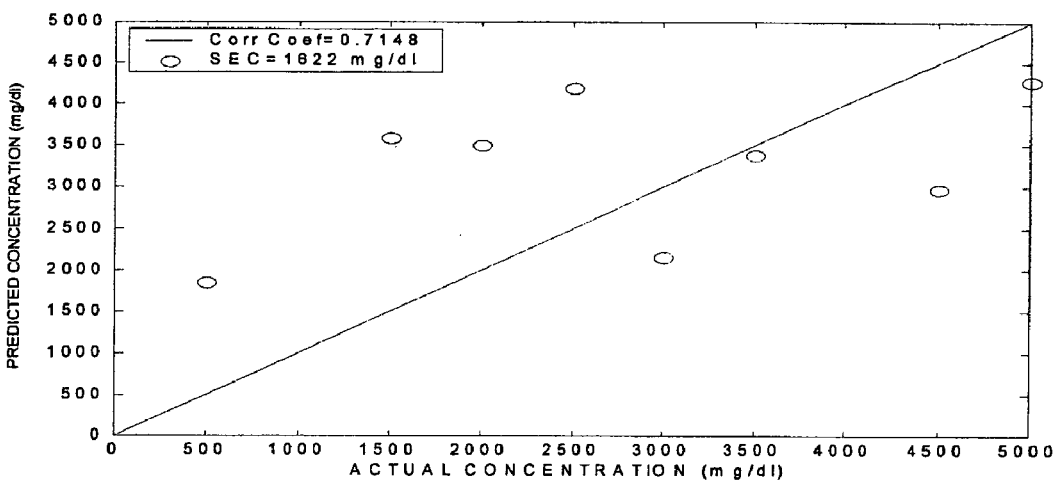
Figure 11C:
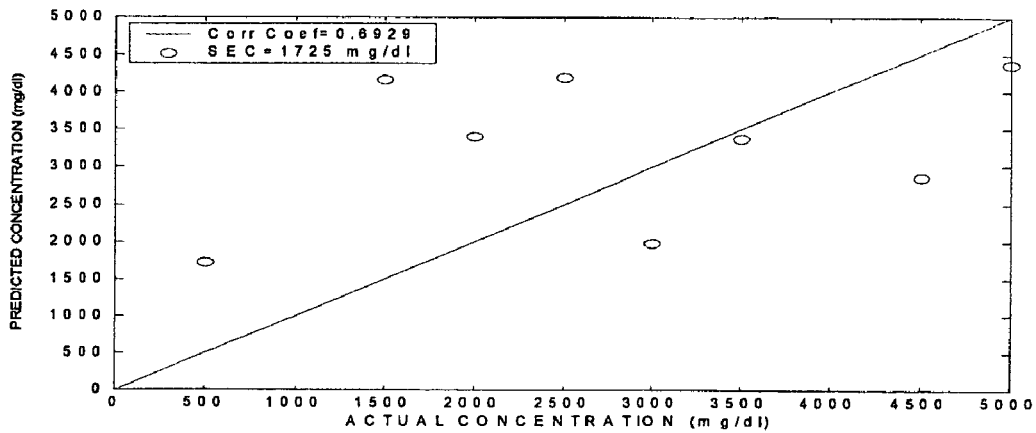
Figure 12A:
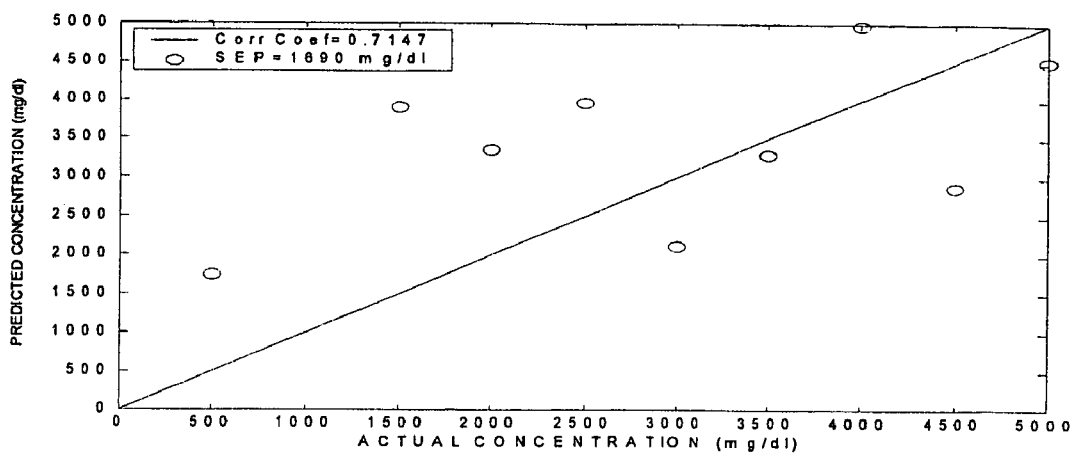
FIGS. 12a, 12b, and 12c are validation graphs for uncompensated glucose-doped water experiments (a)–(c).
Figure 12B:
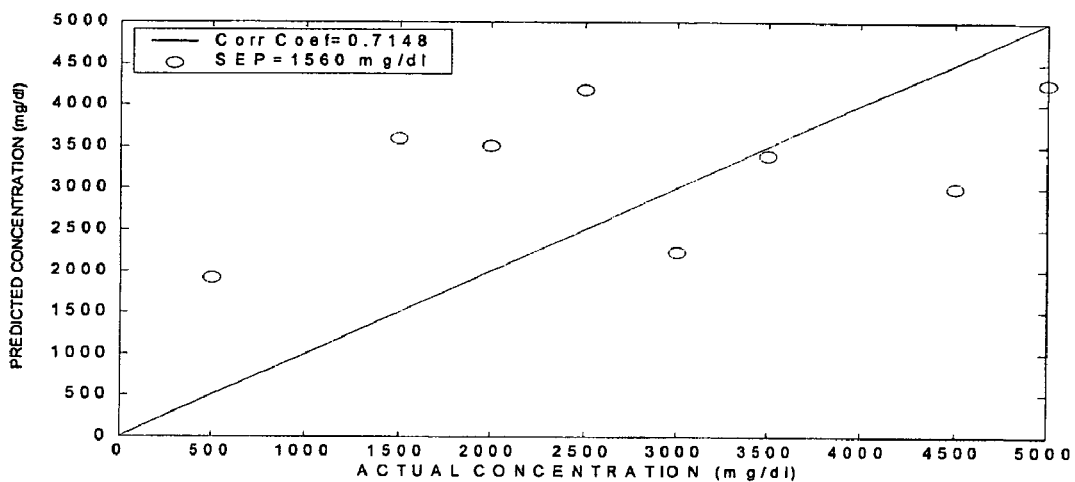
Figure 12C:
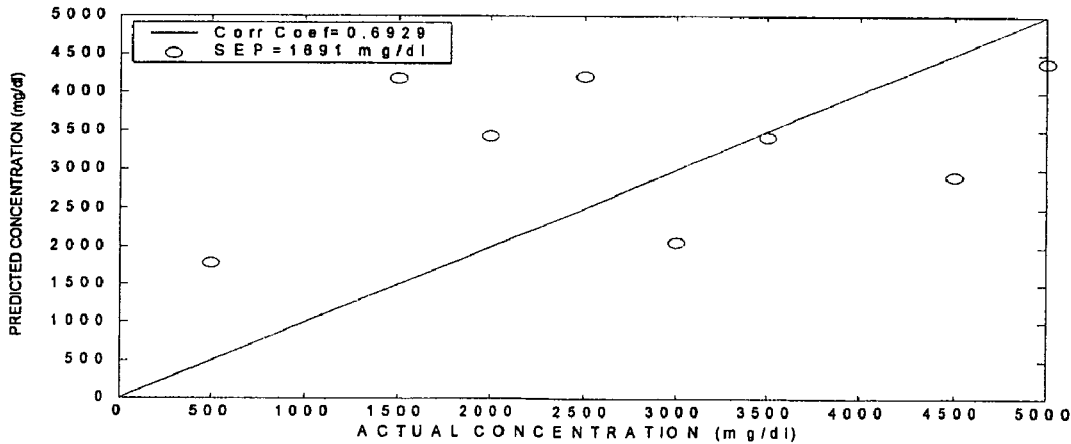
Figure 13A:
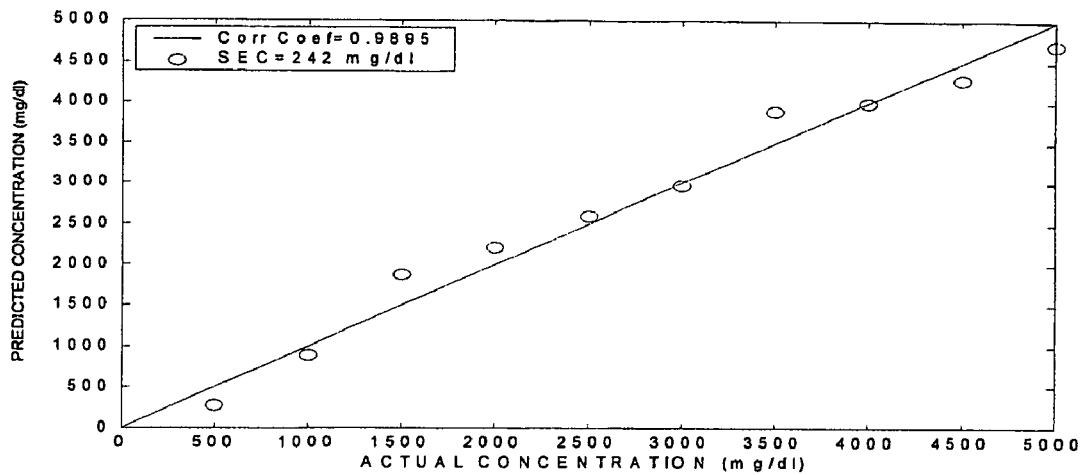
FIGS. 13a, 13b, and 13c are calibration graphs for the compensated glucose-doped water experiments (a)–(c).
Figure 13B:
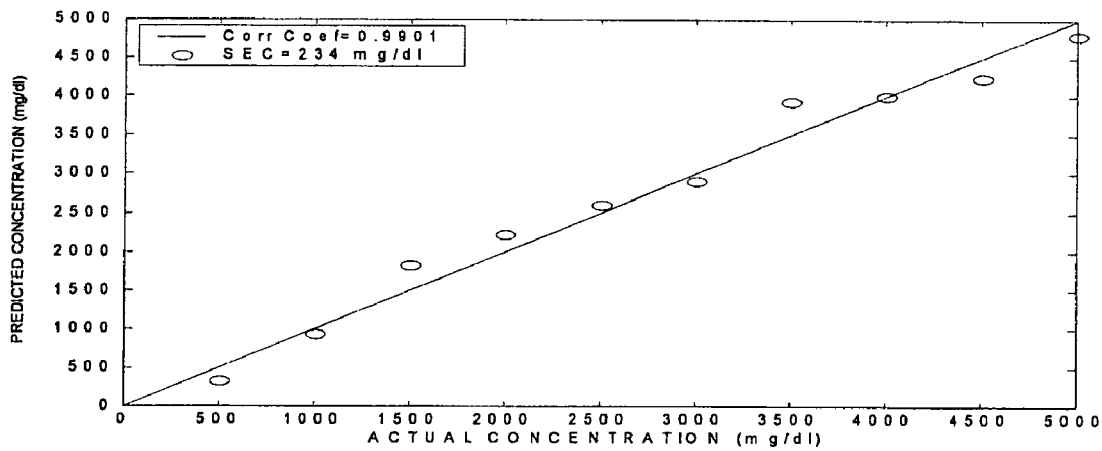
Figure 13C:
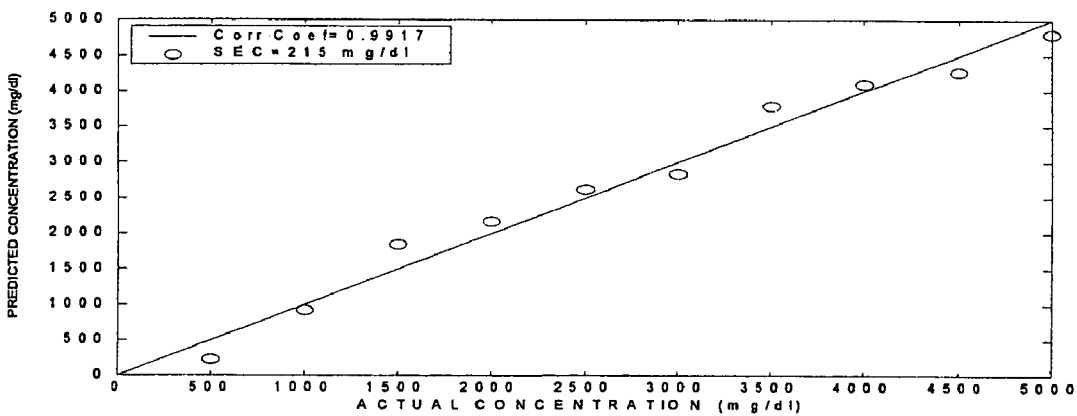
Figure 14A:
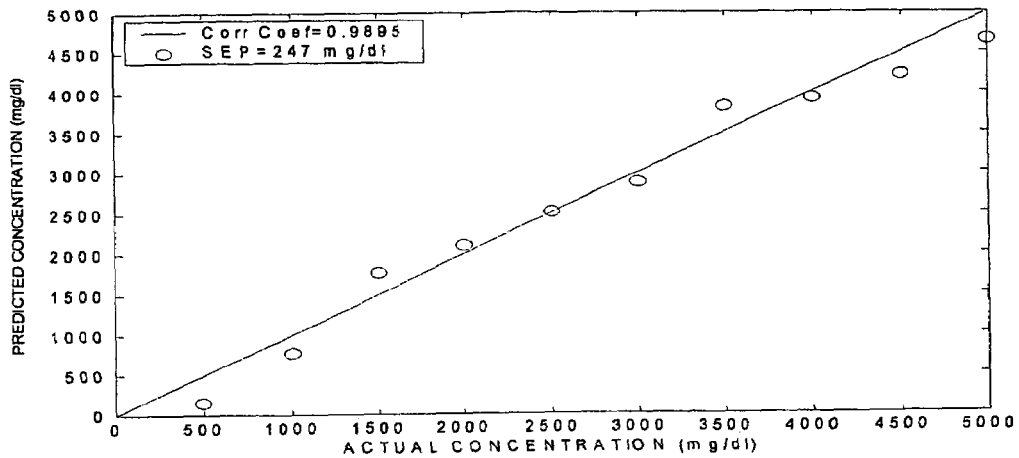
FIGS. 14a, 14b, and 14c are validation graphs for compensated glucose-doped water experiments (a)–(c).
Figure 14B:
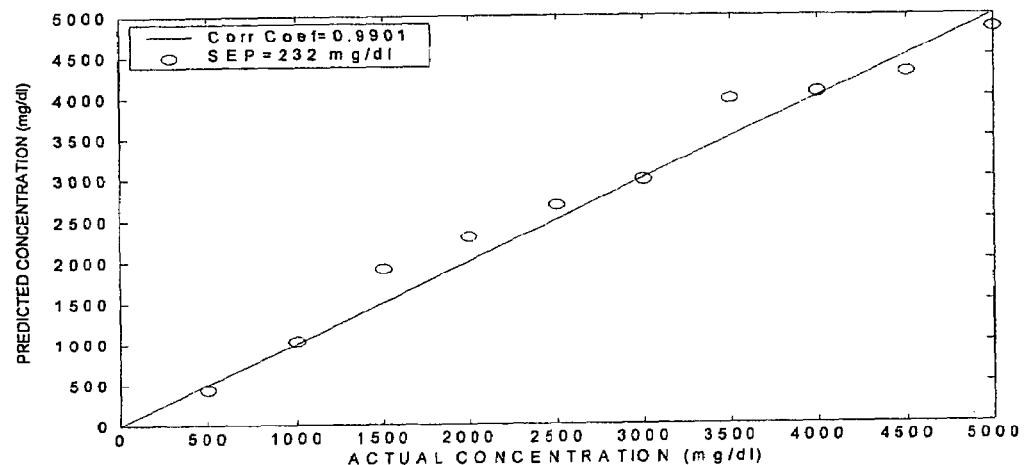
Figure 14C:
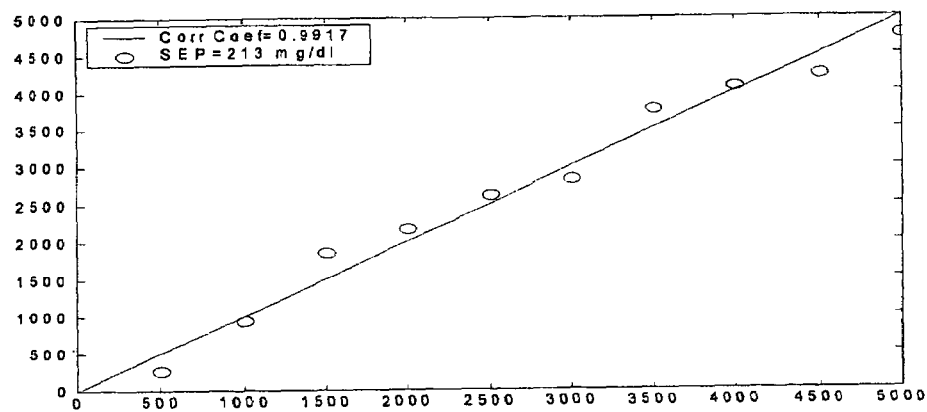

The FFT plots in FIGS. 10a–c illustrate how corneal birefringence masks the signature of glucose. In the FIGS. 10a and 10b, it is seen that a change in glucose concentration changes the magnitude of the detected signal at the modulation frequency (i.e. signal component at 1058 Hz). FIG. 10a corresponds to 0 mg/dl glucose concentration and FIG. 10b corresponds to 200 mg/dl glucose concentration. It should be noted, however, the magnitude at twice the modulation frequency (i.e. 2116 Hz) remains constant which is consistent with eqn 9. As illustrated in FIG. 10c, with maintaining the glucose concentration at 200 mg/dl, however, inducing 5 degrees of corneal retardance, it is seen that when birefringence is induced, the magnitude at the modulation frequency (i.e. 1058 Hz) in comparison with FIG. 10b changes, therefore in essence masking the signature of glucose.

EXAMPLE

Experimental Results with the Designed Corneal Birefringence Compensation System Using the designed corneal birefringence compensated glucose sensing system and the method described herein, three sets of experiments each, one without birefringence compensation and one after birefringence compensation were performed with a glucose concentration range of 0–5000 mg/dl in steps of 500 mg/dl. Sample birefringence values between 3λ/4 and λ were chosen in small increments.

The uncompensated and compensated data obtained is illustrated in Table 1 below.

TABLE 1

| Glucose Concentration | Uncompensated data (Voltage) | | | Compensated data (Voltage) | | |
|---|---|---|---|---|---|---|
| (mg/dl) | Set 1 | Set 2 | Set 3 | Set 1 | Set 2 | Set 3 |
| 0 | 2.075 | 2.025 | 1.997 | 3.54 | 3.5 | 3.466 |
| 500 | 0.952 | 0.93 | 0.942 | 3.394 | 3.35 | 3.365 |
| 1000 | 1.67 | 1.598 | 1.59 | 3.226 | 3.187 | 3.182 |
| 1500 | 0.42 | 0.5 | 0.35 | 2.956 | 2.941 | 2.935 |
| 2000 | 0.557 | 0.52 | 0.535 | 2.862 | 2.835 | 2.847 |
| 2500 | 0.405 | 0.35 | 0.343 | 2.754 | 2.731 | 2.725 |
| 3000 | 0.862 | 0.851 | 0.876 | 2.65 | 2.648 | 2.667 |
| 3500 | 0.571 | 0.55 | 0.54 | 2.397 | 2.37 | 2.412 |
| 4000 | 0.157 | 0.14 | 0.125 | 2.369 | 2.35 | 2.33 |
| 4500 | 0.671 | 0.652 | 0.665 | 2.288 | 2.284 | 2.283 |
| 5000 | 0.27 | 0.33 | 0.302 | 2.168 | 2.132 | 2.14 |

The first three sets of experiments were performed without compensation to show the effect of corneal birefringence. The calibration and validation graphs for the uncompensated data sets are shown in FIGS. 11a–c and FIGS. 12a–c, respectively. Validation of the calibration models for the uncompensated data was performed using the other data sets as independent data sets. By using the least squares calibration model, the computed slope is -4148 and the intercept is 5617. As can be seen from Table 2 below, the uncompensated data set possesses a very low degree of linearity with the mean correlation coefficient r=0.7074. The mean SEC and SEP are 1656 mg/dl and 1647 mg/dl, respectively.

Using the method described herein, the second three sets of experiments were performed with birefringence compensation. Validation of the calibration models for the uncompensated data was performed using the other data sets as independent data sets. The calibration and validation graphs for the compensated data are shown in FIGS. 13a–c and FIGS. 14a–c, respectively. For the designed system and the least squares calibration model, the computed slope is -3731 and the intercept is 12796. As can be seen in Table 2, each data set possesses a high degree of linearity with all correlation coefficients exceeding 0.9894. The mean SEC and SEP for the compensated data are 228 mg/dl and 230 mg/dl, respectively.

TABLE 2

Summary statistics for the collected data sets

| Data | Model | Correlation Coefficient (r) | Standard error of calibration (mg/dl) | Standard error of validation (mg/dl) |
|---|---|---|---|---|
| Uncompensated data | a | 0.7147 | 1623 | 1690 |
|  | b | 0.7148 | 1622 | 1560 |
|  | c | 0.6929 | 1725 | 1691 |
| Compensated data | a | 0.9895 | 242 | 247 |
|  | b | 0.9901 | 234 | 232 |
|  | c | 0.9917 | 215 | 213 |

The compensated data unlike the uncompensated data possesses a high degree of linearity with the correlation coefficient exceeding r=0.9890 for both calibration and validation. Also, there is a 7-fold drop in the SEC and SEP after compensation. These data and results demonstrate the described birefringence compensation technique and the benefits of using such a method in polarimetric glucose measurements.

OTHER EMBODIMENTS

The device described in the attached documents depict only one form in which the applied theoretical approach to corneal birefringence compensation may be realized. It is to be understood that other embodiments of the present invention include the use of other approaches, such as, but not limited to the following, and that such approaches are within the contemplated scope of the present invention:
1) Other optical mechanisms and approaches for the control and handling of polarized light (e.g. instead of using liquid crystal variable retarders, other similar methods to control of polarized light could be through the mechanical movement of optical elements such as fixed retarders, photoelastic modulation, the Pockels effect, etc . . . )
2) The control algorithms for the corneal birefringence compensator could be implemented in a variety of forms, such as, through the use of a proportional integral differential (PID) controller or by other similar methods.
3) The birefringence compensator could be extended through other methods as described in (1) to provide enhanced and more robust control to achieve birefringence compensation (e.g. extension from single axis, as described, to three-axis birefringence compensation).
4) The birefringence analyzer could be extended to more fully characterize the state of polarized light to provide feedback to other implementations of the birefringence compensator (e.g. a three-axis variable birefringence compensator).

The above descriptions of the preferred and alternative embodiments of the present invention are intended to be illustrative and are not intended to be limiting upon the scope and content of the following claims.

All of the compositions and methods disclosed and claimed herein can be made and executed without undue experimentation in light of the present disclosure. While the compositions and methods of this invention have been described in terms of the foregoing illustrative embodiments, it will be apparent to those skilled in the art that variations, changes, modifications, and alterations may be applied to the compositions and/or methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

I claim:

1. A noninvasive birefringence-based retardance compensated sensing polarimeter used to measure and compensate for birefringence when measuring levels of an optically active substance in a sample comprising:
an optical birefringence analyzer configured to sense real-time birefringence-based retardance contributions in a signal obtained from a sample and configured to provide a feedback signal to a compound electro-optical system, and
a compound electro-optical system configured to receive the signal from the birefringence analyzer and configured to negate the retardance in the signal obtained from the sample.

2. A polarimeter according to claim 1 wherein the sample is a patient's eye or other associated tissue.

3. A polarimeter according to claim 1 wherein the sample is aqueous humor of a patient's eye.

4. A polarimeter according to claim 1 wherein the sample is tissue from a thin-skin area of a patient.

5. A polarimeter according to claim 1 wherein the sample is tissue from a patient's ear, nose or thin skin between fingers or toes.

6. A polarimeter according to claim 1 wherein the compound electro-optical system further includes an analyzer having at least one Faraday modulator, at least one Faraday compensator, at least one analyzer, at least one detector, at least one amplifier, and at least one controller.

7. A polarimeter according to claim 1 wherein the optical birefringence analyzer comprises at least one circular analyzer, at least one detector and at least one controller.

8. The system of claim 1, wherein the optically active substance is glucose in an animal's eye.

9. A noninvasive birefringence-based retardance compensated sensing polarimeter used to measure and compensate for birefringence when measuring levels of an optically active substance in a sample comprising:
an optical birefringence analyzer configured to sense real-time birefringence-based retardance contributions in a signal obtained from a sample and configured to provide a feedback signal to a compound electro-optical system, and
a compound electro-optical system configured to receive the signal from the birefringence analyzer and configured to negate the retardance in the signal obtained from the sample,
wherein the birefringence analyzer includes a means for measuring birefringence present in the sample, and
wherein the compound electro-optical system includes a means for computing a value of retardance that needs to be applied as birefringence compensation in order to determine the optical rotation polarization vector due to the sample.

10. The polarimeter of claim 9, wherein the sample comprises one or more of a patient's eye or other associated tissue, including aqueous humor; and, tissue from a thin-skin area of the patient, including tissue from the patient's ear, nose or thin skin between fingers or toes.

11. The polarimeter of claim 9, wherein the sample comprises glucose.

12. A noninvasive birefringence-based retardance sensing polarimeter comprising a means for measuring optical polarization rotation of a substance in a sample, a means for computing the value of retardance that needs to be applied to a birefringence compensator in order to eliminate any birefringence contribution due to a sample, and means for eliminating birefringence contribution due to the sample.

13. The polarimeter of claim 12, wherein the sample comprises one or more of a patient's eye or other associated tissue, including aqueous humor;
  and, tissue from a thin-skin area of the patient, including tissue from the patient's ear, nose or thin skin between fingers or toes.

14. The polarimeter of claim 12, wherein the sample comprises glucose.

15. A noninvasive birefringence sensing polarimeter system for measuring a presence of an optically active substance in a sample comprising:
  at least one light source,
  at least one polarizer,
  at least one birefringence compensator that applies a retardance that cancels out any effect due to birefringence-based retardance,
  at least one beam splitter,
  at least one means for measuring optical polarization rotation caused by the presence of the optically active substance, and
  at least one means for computing the value of retardance that needs to be applied to the at least one birefringence compensator.

16. The system of claim 15, wherein the at least one means for measuring optical polarization rotation comprises at least one Faraday modulator, at least one Faraday compensator, at least one analyzer, at least one detector, at least one amplifier, and at least one controller.

17. The system of claim 15, wherein the at least one means for computing the value of retardance that needs to be applied to the at least one birefringence compensator comprises at least one circular analyzer, at least one detector, and at least one controller.

18. The system of claim 17 wherein the value of retardance is computed and sent as an input into a compensation portion of the controller wherein a compensation algorithm can be represented by a difference equation where the retardance applied by the birefringence compensator is the computed value of retardance, and wherein upon completion, there is no circularly polarized component and only linearly polarized light and any birefringence is compensated for.

19. The system of claim 15, wherein the sample comprises one or more of a patient's eye or other associated tissue, including aqueous humor; and, tissue from a thin-skin area of the patient, including tissue from the patient's ear, nose or thin skin between fingers or toes.

20. The system of claim 15, wherein the sample comprises glucose.

21. A noninvasive birefringence sensing polarimeter system for measuring a presence of an optically active substance in a sample comprising:
  at least one light source,
  at least one polarizer,
  at least one birefringence compensator that applies a retardance that cancels out any effect due to birefringence-based retardance,
  at least one beam splitter,
  at least one means for measuring optical polarization rotation caused by the presence of the optically active substance, and
  at least one means for computing the value of retardance that needs to be applied to the at least one birefringence compensator,
  wherein the at least one means for computing the value of retardance that needs to be applied to the at least one birefringence compensator comprises at least one circular analyzer, at least one detector, and at least one controller, and
  wherein the value of retardance ($\delta$) is computed from the equation:

$$\delta_{predicted} = \sin^{-1}\left[\frac{-2V}{\sin(2\gamma)}\right]$$

wherein 'V' is the Stokes parameter 'V' and '$\gamma$' is the azimuthal angle.

22. The system of claim 21, wherein the sample comprises one or more of a patient's eye or other associated tissue, including aqueous humor; and, tissue from a thin-skin area of the patient, including tissue from the patient's ear, nose or thin skin between fingers or toes.

23. The system of claim 21, wherein the sample comprises glucose.

24. A noninvasive birefringence sensing polarimeter system for measuring a presence of an optically active substance in a sample comprising:
  at least one light source,
  at least one polarizer,
  at least one birefringence compensator that applies a retardance that cancels out any effect due to birefringence-based retardance,
  at least one beam splitter,
  at least one means for measuring optical polarization rotation caused by the presence of the optically active substance, and
  at least one means for computing the value of retardance that needs to be applied to the at least one birefringence compensator,
  wherein the at least one means for computing the value of retardance that needs to be applied to the at least one birefringence compensator comprises at least one circular analyzer, at least one detector, and at least one controller,
  and wherein the value of retardance is computed and sent as an input into a compensation portion of the controller wherein a compensation algorithm can be represented by the difference equation
  y(n)=x(n)+y(n−1), where 'y' is the retardance applied by the birefringence compensator and 'x' is the value of computed retardance, and wherein upon completion of the computed value of retardance, there is no circularly polarized component and only linearly polarized light and any birefringence is compensated for.

25. The system of claim 24, wherein the sample comprises one or more of a patient's eye or other associated tissue, including aqueous humor; and, tissue from a thin-skin area of the patient, including tissue from the patient's ear, nose or thin skin between fingers or toes.

26. The system of claim 24, wherein the sample comprises glucose.

27. A corneal birefringence compensated sensing system for measuring a presence of an optically active substance in a patient's eye comprising:
a polarizer configured to be aligned with i) at least one optic axis of the patient's anterior corneal surface to minimize effects of anterior corneal birefringence, wherein a laser emits a polarized laser beam configured to pass through the patient's cornea, and ii) a posterior retarder with a retardance ($\delta$),
a beam splitter wherein, in order to compensate for any corneal birefringence before determining rotation of the optically active substance in the patient's eye, an output light from the patient's eye and the posterior retarder is separated into two paths by the beam splitter such that:
one beam is passed through an analyzer capable of characterizing at least one of the four Stokes parameters (I,Q,U,V), and
a second of the beams is received by a modulator capable of modulating a linear polarization vector of the laser beam and compensating for any retardance-based contribution found in the patient's eye.

28. The system of claim 27, wherein the sample comprises glucose.

29. A birefringence compensation system comprising:
1) a light source,
2) a polarizer for polarizing a light beam from the light source and for orienting the beam such that maximum transmission is obtained, wherein the polarizer is aligned with
3) an optic axis of an initial retarder, which minimizes the effect of any birefringence in a given sample,
4) an electro-optical retarder that accounts for any birefringence which induces a phase retardance ($\delta$) in the polarized light beam resulting in a change in the state of polarization from linearly polarized light to elliptically polarized light,
5) a birefringence compensator for applying a retardance that cancels out any effect due to the birefringence,
6) a non-polarizing beam splitter for splitting the elliptically polarized light into two beams,
7) a circular analyzer which receives a first of the split beams, wherein the circular analyzer comprises a quarter wave plate followed by a 45° linear polarizer, capable of characterizing the circularly polarized Stokes parameter 'V',
8) a silicon photo diode detector which receives the first directed beam,
9) a feedback controller for receiving as input an output from the detector, whereby the retardance is computed and sent as an input into a compensation portion of the controller wherein a compensation algorithm can be represented by the difference equation y(n)=x(n)+y(n−1) where 'y' is the retardance applied by the birefringence compensator and 'x' is the computed retardance such that, upon completion of the computed value of retardance, there is no circularly polarized component and only linearly polarized light and any birefringence is compensated for;
10) a Faraday modulator for receiving a second of the split beams and for modulating the linear polarization vector of the light;
11) a Faraday compensator for providing feedback compensation by nullifying or eliminating any rotation of the polarization vector due to the sample,
12) an analyzer having its transmission axis oriented perpendicular to that of the polarizer, the analyzer transforming the modulated polarization vector into intensity modulation according to Malus' law,
13) a silicon photo diode detector which receives the directed second beam and which provides an output comprising a voltage proportional to a detected light intensity,
14) a wide bandwidth amplifier for amplifying the output of the detector,
15) a lock-in amplifier and controller for receiving an amplified output from the wide bandwidth amplifier whereby the lock-in amplifier measures the signal component present at the modulation frequency, while rejecting low and high frequency electro-magnetic noise, and
16) a power supply wherein an output of the controller is applied to the Faraday compensator through the power supply such that, upon completion, the output voltage of the controller is proportional to the concentration of the sample.

30. The system of claim 29 wherein the sample contains an optically active substance.

31. The system of claim 29, wherein the sample contains glucose or other optically active molecule(s).

32. The system of claim 29 wherein a value of retardance ($\delta$) is computed from the equation:

$$\delta_{predicted} = \sin^{-1}\left[\frac{-2V}{\sin(2\gamma)}\right]$$

wherein 'V' is the Stokes parameter 'V' and '$\gamma$' is the azimuthal angle.

33. A method for noninvasive birefringence sensing used to measure and compensate for birefringence when measuring levels of an optically active substance in a sample comprising the steps of:
sensing real-time birefringence-based retardance contributions in a signal obtained from a sample;
providing a feedback signal to a compound electro-optical system,
said electro-optical system receiving the signal from the birefringence analyzer and negating the birefringence-based retardance contributions found in the signal obtained from the sample.

34. A method according to claim 33 wherein the sensing is performed by an optical birefringence analyzer, the sample is a patient's eye, the birefringence-based retardance contributions are corneal birefringence-based retardance contributions, and further including the steps: measuring corneal birefringence-based retardance contributions, and determining an optical rotation polarization vector due to the sample.

35. The method of claim 33, wherein the sample comprises one or more of a patient's eye or other associated tissue, including aqueous humor; and, tissue from a thin-skin area of the patient, including tissue from the patient's ear, nose or thin skin between fingers or toes.

36. The method of claim 33, wherein the sample comprises glucose.

37. A method for noninvasive birefringence sensing comprising the steps: measuring birefringence present in a sample, computing a
value of retardance that needs to be applied as birefringence compensation in order to determine the optical rotation polarization vector due to any optical activity of the sample, and compensating for birefringence-based retardance based upon said computed value.

38. The method system of claim 37, wherein the sample comprises one or more of a patient's eye or other associated tissue, including aqueous humor; and, tissue from a thin-skin area of the patient, including tissue from the patient's ear, nose or thin skin between fingers or toes.

39. The method of claim 37, wherein the sample comprises glucose.

40. A method for overcoming corneal birefringence comprising: compensating for birefringence-based retardance of a cornea in a signal using a circular Stokes parameter 'V', and measuring glucose concentration with the compensated signal using a Faraday based glucose sensing polarimeter.

41. A non-invasive retardance-based in vivo method for sensing a concentration of an optically active substance in an animal's eye wherein the method comprises the steps of:
    aligning a polarizer with at least one optic axis of an anterior corneal surface to minimize effects of anterior corneal birefringence and emitting a polarized laser beam through the animal's eye with an overall retardance ($\delta$), and
    splitting the laser beam wherein, in order to compensate for the a posterior birefringence before determining rotation of the optically active substance, output light from the animal's eye and retarder is separated into two paths by a beam splitter, further including
    characterizing at least one of four Stokes parameters (I,Q,U,V) of a first of said beams, and
    modulating a linear polarization vector of a second of said beams.

42. The method of claim 41, wherein the sample comprises glucose.

43. A non-invasive in vivo method for sensing a concentration of an optically active substance in a sample comprising the steps, in sequence of:
    providing at least one beam of light,
    passing the at least one beam through at least one polarizer,
    passing the at least one beam through at least one sample,
    passing the at least one beam through at least one birefringence compensator,
    passing the at least one beam through at least one beam splitter to divide the at least one beam into at least two beams of light,
    measuring for rotation of the optically active substance by passing at least one split beam of light through at least one Faraday modulator, at least one compensation Faraday rotator, at least one analyzer, and at least one detector, and
    computing the value of retardance that needs to be applied at the at least one birefringence compensator by passing at least one of the split beams of light through a circular analyzer, a detector, and a controller,
    operating the birefringence compensator in response to the computed value of retardance wherein there is no circularly polarized component and only linearly polarized light and birefringence is compensated for.

44. The method system of claim 43, wherein the sample comprises one or more of a patient's eye or other associated tissue, including aqueous humor; and, tissue from a thin-skin area of the patient, including tissue from the patient's ear, nose or thin skin between fingers or toes.

45. A noninvasive birefringence sensing polarimeter comprising means for measuring optical polarization rotation of a substance in a sample, means for computing a value of retardance that needs to be applied to a birefringence compensator in order to eliminate any birefringence contribution due to a sample, and means for eliminating the birefringence contribution due to the sample that includes an anterior birefringence compensator and a posterior birefringence compensator.

46. The polarimeter of claim 45, wherein the sample comprises one or more of a patient's eye or other associated tissue, including aqueous humor; and, tissue from a thin-skin area of the patient, including tissue from the patient's ear, nose or thin skin between fingers or toes.

47. The polarimeter of claim 45, wherein the sample comprises glucose.

48. A noninvasive birefringence compensated sensing polarimeter used to measure and compensate for birefringence when measuring levels of an optically active substance in a sample comprising:
    an anterior birefringence compensator configured to sense real-time birefringence contributions in a signal and configured to provide a first feedback signal to a compound electro-optical system,
    a posterior birefringence compensator configured to sense real-time birefringence contributions in the signal and configured to provide a second feedback signal to a compound electro-optical system, and
    a compound electro-optical system configured to receive the first signal from the anterior birefringence compensator and the second signal from the posterior birefringence compensator, and configured to negate the birefringence contributions found in the signal.

49. A birefringence sensing polarimeter according to claim 48 wherein the birefringence compensators include a means for measuring birefringence present in the sample, and wherein the compound electro-optical system includes a means for computing a value of retardance that needs to be applied as birefringence compensation in order to determine an optical rotation polarization vector due to the sample.

50. The polarimeter of claim 48, wherein the sample comprises one or more of a patient's eye or other associated tissue, including aqueous humor; and, tissue from a thin-skin area of the patient, including tissue from the patient's ear, nose or thin skin between fingers or toes.

51. The polarimeter of claim 48, wherein the sample comprises glucose.

52. A noninvasive birefringence sensing polarimeter system comprising:
    at least one light source,
    at least one polarizer,
    at least one anterior birefringence compensator that applies a retardance that cancels out any effect due to anterior birefringence in at least one signal obtained from a sample containing a substance to be measured,
    at least one posterior birefringence compensator that applies a retardance that cancels out any effect due to posterior birefringence,
    at least one means for measuring optical polarization rotation of the sample, and at least one means for computing a value of retardance that needs to be applied to the birefringence compensators.

53. The system of claim 52 wherein at least one means for computing the value of retardance that needs to be applied to the birefringence compensators comprises at least one circular analyzer, at least one detector, and at least one controller.

54. The system of claim 53 wherein the system is a three-axis birefringence compensator and the value of retardance is computed and sent as an input into a compensation portion of the at least one controller to negate sample birefringence effects.

55. The system of claim 52, wherein the sample comprises one or more of a patient's eye or other associated tissue, including aqueous humor; and, tissue from a thin-skin area of the patient, including tissue from the patient's ear, nose or thin skin between fingers or toes.

56. The system of claim 52, wherein the sample comprises glucose.

57. A noninvasive birefringence sensing polarimeter system comprising:
   at least one light source,
   at least one polarizer,
   at least one anterior birefringence compensator that applies a retardance that cancels out any effect due to anterior sample birefringence in at least one signal obtained from a sample containing a substance to be measured,
   at least one posterior birefringence compensator that applies a retardance that cancels out any effect due to posterior sample birefringence, and
   at least one means for measuring optical polarization rotation of a sample.

58. The system of claim 57 further including at least one means for compensating for the sample birefringence wherein both the anterior and posterior birefringence compensators are modulated at different frequencies and operated in an open-loop approach.

59. The system of claim 57, wherein the sample comprises one or more of a patient's eye or other associated tissue, including aqueous humor; and, tissue from a thin-skin area of the patient, including tissue from the patient's ear, nose or thin skin between fingers or toes.

60. The system of claim 57, wherein the sample comprises glucose.

* * * * *